US007056728B2

(12) United States Patent
Francis et al.

(10) Patent No.: US 7,056,728 B2
(45) Date of Patent: Jun. 6, 2006

(54) COMPOSITIONS AND METHODS FOR USE THEREOF IN MODIFYING THE GENOMES OF MICROORGANISMS

(75) Inventors: Kevin P. Francis, Alameda, CA (US); Anthony F. Purchio, Alameda, CA (US)

(73) Assignee: Xenogen Corporation, Alameda, CA (US)

( * ) Notice: Subject to any disclaimer, the term of this patent is extended or adjusted under 35 U.S.C. 154(b) by 262 days.

(21) Appl. No.: 09/888,049

(22) Filed: Jun. 21, 2001

(65) Prior Publication Data

US 2002/0137215 A1 Sep. 26, 2002

Related U.S. Application Data

(60) Provisional application No. 60/274,105, filed on Mar. 7, 2001, provisional application No. 60/216,257, filed on Jul. 6, 2000.

(51) Int. Cl.
C12N 15/00 (2006.01)
C12N 15/01 (2006.01)
C12N 15/74 (2006.01)

(52) U.S. Cl. .......................... 435/320.1; 435/4; 435/6; 435/440; 435/471; 435/473; 435/477; 435/243; 435/252.3; 536/23.1; 536/24.1

(58) Field of Classification Search ............... 536/23.1, 536/24.1; 435/4, 6, 440, 471, 473, 477, 320.1, 435/243, 252.3
See application file for complete search history.

(56) References Cited

U.S. PATENT DOCUMENTS

| 5,399,496 | A | * | 3/1995 | Fujiwara et al. ........... 435/69.1 |
| 5,591,601 | A | * | 1/1997 | Wagner et al. ............. 435/69.1 |
| 5,650,135 | A | | 7/1997 | Contag et al. |
| 5,900,362 | A | | 5/1999 | Eberz et al. |
| 6,020,121 | A | | 2/2000 | Bao et al. |
| 6,110,661 | A | * | 8/2000 | Lajoie et al. .................. 435/4 |
| 6,217,847 | B1 | | 4/2001 | Contag et al. |
| 6,329,160 | B1 | * | 12/2001 | Schneider et al. ......... 435/7.31 |

FOREIGN PATENT DOCUMENTS

| EP | 0 639 641 A | 2/1995 |
| EP | 1 016 419 | 7/2000 |
| WO | WO 90/04041 | 4/1990 |
| WO | WO 93/16172 | 8/1993 |
| WO | WO 96/40979 A1 | 12/1996 |
| WO | WO 97/11690 A2 | 4/1997 |
| WO | WO 97/11690 A3 | 4/1997 |
| WO | WO 97/18841 | 5/1997 |
| WO | WO 97/40381 S1 | 10/1997 |
| WO | WO 99/14311 | 3/1999 |
| WO | WO 00/36106 | 6/2000 |
| WO | WO 01/18195 A2 | 3/2001 |
| WO | WO 01/18225 A1 | 3/2001 |
| WO | WO 01/37195 A2 | 5/2001 |

OTHER PUBLICATIONS

Knudtson et al. Gene 137: 217-222, 1993.*
Baldwin et al. Biochemistry 29:5509-5515, 1990.*
Definition of "overlapping" as provided by Merriam Wesbster OnLine.*
Definition of "commensurate" as provided by Merriam Wesbster OnLine.*
Definition of "derivative" as provided by Merriam Wesbster OnLine.*
Birch et al. Journal of General Microbiology 131:1299-1300, 1985.*
Hahn, T., et al., "Construction and Analysis of Modified Tn*4001* Conferring Chloramphenicol Resistance in Mycoplasma *Pneumoniae,*" *Plasmid 41:*120-124 (1999).
Jacobs et al., "Highly Bioluminescent *Bacillus subtilis* Obtained Through High-level Expression of a *luxAB* Fusion Gene," *Mol. Gen. Genet 230:*251-256 (1991).
Phillips-Jones, M.K. "Bioluminescence (*lux*) Expression in the Anaerobe *Clostridium perfringens,*" *FEMS Microbiology Letters* 106:265-270 (1993).
Loimaranta, et al., "Generation of Bioluminescent *Steptococcus mutans* and Its Usage in Rapid Analysis of the Efficacy of Antimicrobial Compounds" *Antimicrobial Agents and Chemotherapy* 42(8):1906-1910 (1998).
Meighen, E.A., "Bacterial Bioluminescence: Organization, Regulation, and Application of the *lux* Genes," *BASEB Journal* 7(11):1016-1022 (1993).
O'Connell, K.P., et al., "Identification of Cold Shock Gene Loci in *Sinorhizobium melilot* by Using a *luxAB* Reporter Transposon," *Appl. Environ. Microbiol.* 66(1):401-405 (2000).
Roy, G., et al., "Episomal and Stable Expression of the Luciferase Reporter Gene for Quantifying *Leishmania* SPP. Infections in Macrophages and in Animal Models," *Molecular and Biochemical Parasitology* 110:*195-206 (2000).
Sibakov, M., et al., "Secretion of TEM β-Lactamase with Signal Sequences Isolated from the Chromosome of *Lactococcus lactis* subsp. *lactis,*" *Appl. Environ. Microbiology* 57(2):341-348 (1991).

(Continued)

*Primary Examiner*—James Ketter
*Assistant Examiner*—David A. Lambertson
(74) *Attorney, Agent, or Firm*—Robins & Pasternak LLP

(57) ABSTRACT

The present invention relates to bacterial luciferase transposon cassettes suitable for conferring bioluminescence properties on a Gram-positive bacteria, Gram-negative bacteria, and other organisms of interest. The invention further includes cells transformed with vectors carrying the transposon cassettes, cells whose genomes have been modified by introduction of such cassettes, and methods of making and using such transposon cassettes, transposon cassette vectors, and cells containing the transposons.

22 Claims, 9 Drawing Sheets

OTHER PUBLICATIONS

Sohaskey et al., "Construction and Application of Plasmid- and Transposon-Based Promoter-Probe Vectors for *Streptomyces* ssp. That Employ a *Vibrio harveyi* Luciferase Reporter Cassette," *Journal of Bacteriology* 174(2):367-376 (1992).

Steidler, et al., "The Expression of *Photinus pyralis* Luciferase Gene in *Staphylococcus aureus* Cowan I allows the Development of a Live Amplifiable Tool for Immunodetection" Applied and Environmental Microbiology 62(7):2356-2359 (1996).

Steinmann, et al., "Saturation Mutagenesis in *Escherichia coli* of a Cloned *Xanthomonas campestris* DNA Fragment with the *lux* Transposon Tn4431 Using the Delivery Plasmid pDS1, Thermosensitive in Replication," *Appl. Microbiol. Biotechnol.* 40:356-360 (1993).

Ulitzur, S., J. 'Established Technologies and New Approaches in Applying Luminous Bacteria for Analytical Purposes," Biolumin Chemilumin. 12:179-92 (1997).

Zhang et al., "Bioluminescence for Biological Sensing in Living Mammals," *Oxygen Transport to Tissue XXI*, edited by Eke and Delpy. Kluwer Academic/Plenum Publishers, New York, (1999).

Francis et al., "Monitoring Bioluminescent *Staphylococcus aureus* Infections in Living Mice Using a Novel LuxABCDE Construct," *Infection and Immunity* 68(6):3594-3600 (2000).

Kozlowski et al., "Vectors Permitting Visual Monitoring of Simple Transposition Events," *Gene* 80(2):217-225 (1989).

Lunsford, Dwayne R., "A Tn4001 Delivery System for *Streptococcus Gordonil*," *Plasmid* 33(2):153-157 (1995).

Bianchi et al., "Stress Responses as a Tool to Detect and Characterize the Mode of Action of Antibacterial Agents," *Applied and Environmental Microbiology* 65(11):5023-5027 (1999).

Lingnau et al., "Expression of the Listeria *Monocytogenes* EGD *inlA* and *inlB* Genes, Whose Products Mediate Bacterial Entry into Tissue Culture Cell Lines, by PrfA-Dependent and -Independent Mechanisms," *Infection and Immunity* 63(10):3896-3903 (1995).

Loessner et al., "Structural Proteins and DNA Characteristics of 14 *Listeria* Typing Bacteriophases," *Journal of General Virology* 75:701-710 (1994).

Loessner and Scherer, "Organization and Transcriptional Analysis of the *Listeria* Phage A511 Late Gene Region Comprising the Major Capsid and Tail Sheath Protein Genes *cps* and *tsh*," *Journal of Bacteriology* 177(22):6601-6609 (1995).

\* cited by examiner

SEQUENCE LISTING

<160> NUMBER OF SEQ ID NOS: 20

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence:
      Gram-positive ribosome binding site

<400> SEQUENCE: 1 aggagg                                                                    6

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Primer XAF

<400> SEQUENCE: 2
ccccggatcc tgcagatgaa gcaagaggag gactctctat g                 41

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Primer XAR

<400> SEQUENCE: 3
ggcggatccg tcgacttaat ataatagcga acgttg                       36

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Primer XBF

<400> SEQUENCE: 4
gggaattctc gaggaggaga gaaagaaatg aaatttgga                    39

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Primer XBR

<400> SEQUENCE: 5
ggcggatccg tcgacttagg tatattccat gtggtac                      37

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Primer XCF

<400> SEQUENCE: 6
gggaattctc gaggaggatg gcaaatatga ctaa                         34

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Primer XCR

<400> SEQUENCE: 7
ggcggatccg tcgacttatg ggacaaatac aaggaac                      37

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Primer XDF

```
<400> SEQUENCE: 8
gggaattctc gaggaggagt aaaagtatgg aaaatga                              37

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Primer XDR

<400> SEQUENCE: 9
ggcggatccg tcgacttaag acagagaaat tgcttga                              37

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Primer XEF

<400> SEQUENCE: 10
gggaattctc gaggaggaaa acaggtatga cttcatag                             38

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Primer XER

<400> SEQUENCE: 11
ggcggatccg tcgacttaac tatcaaacgc ttcggtta                             38

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Primer
      KanF2

<400> SEQUENCE: 12
ctgtagactc gaggagggaa ataataaatg gc                                   32

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Primer
      KanR2

<400> SEQUENCE: 13
cagagtgtcg acagttgcgg atgtac                                          26

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Primer
      MGC-CAT-F1
```

```
<400> SEQUENCE: 14
ggtgtccctg ttgataccg                                                    19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer
      LuxA-Rev

<400> SEQUENCE: 15
ccacactcct cagagatgcg                                                   20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Primer
      LuxIF3

<400> SEQUENCE: 16
gcttggtaac ccttatgtcg c                                                 21

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Primer
      LuxR3

<400> SEQUENCE: 17
gggaggttgg tatgtaagc                                                    19

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Primer R2

<400> SEQUENCE: 18
cgtttcatta cctctgtttg ag                                                22

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence:  Primer
      M13F

<400> SEQUENCE: 19
gtaaaacgac ggccagt                                                      17

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: CSP1
```

```
<400> SEQUENCE: 20

Glu Met Arg Leu Ser Lys Phe Phe Arg Asp Phe Ile Leu Gln Arg Lys
1               5                   10                  15
Lys
```

COMPOSITIONS AND METHODS FOR USE THEREOF IN MODIFYING THE GENOMES OF MICROORGANISMS

CROSS-REFERENCE TO RELATED APPLICATIONS

This application is related to U.S. Provisional Patent Applications Ser. No. 60/216,257, filed 6, Jul. 2000, and Ser. No. 60/274,105, filed 7, Mar. 2001, from which priority is claimed under 35 USC §119(e)(1), and which applications are incorporated herein by reference in their entireties.

TECHNICAL FIELD

The present invention generally relates to transposon cassettes, methods of making same, and methods of use thereof.

BACKGROUND OF THE INVENTION

Bioluminescent bacteria are widely found in both marine and terrestrial environments. Interestingly, all identified species of naturally occurring marine and terrestrial bioluminescent bacteria are Gram-negative. To date, at least eleven species in four Gram-negative genera have been described: *Vibrio, Photobacterium, Shewanella (Altermonas)* and *Photorhabdus (Xenorhabdus)*. In all these species, the five genes responsible for bioluminescence are clustered in the lux operon (luxCDABE).

The bioluminescence (emitted blue-green light having a wavelength of about 490 nm) is thought to result from a luciferase-catalyzed oxidation of reduced flavin mononucleotide ($FMNH_2$) and a long-chain fatty aldehyde. The luciferase enzyme is encoded by two subunits (luxAB), whereas the fatty acid reductase polypeptides responsible for the biosynthesis of the aldehyde substrate for the luminescent reaction are encoded by the three genes luxCDE. The genes encoding luciferase and the fatty acid reductase polypeptides have been cloned from the lux operons of *Vibrio, Photobacterium* and *Photorhabdus* and sequenced. In each case, the luxCDE genes flank the luxAB genes, with transcription in the order luxCDABE. Although a number of additional lux genes have been identified in each of these three bacteria, only luxA-E are essential for the biosynthesis of light (reviewed by Meighen, E., (1993, *The FASEB Journal* 7:1016–1022 and Ulitzur, S., (1997), *J. Biolumin Chemilumin* 12:179–192).

Methods described in U.S. Pat. No. 5,650,135, make possible the detection of bioluminescent bacteria in a living animal without dissecting or otherwise opening the animal up ("in vivo monitoring")—the light is detected through muscle, skin, fur & other traditionally "opaque" tissues using a highly sensitive camera While a non-bioluminescent Gram-negative bacterium can typically be engineered to have bioluminescence properties by cloning into it a luxCDABE operon (under control of a suitable promoter) from a bioluminescent species (see, e.g., Contag, et al., U.S. Pat. No. 5,650,135), previous attempts to make bioluminescent Gram positive bacteria have met with limited success. For example, one approach employed an expression cassette encoding a functional LuxAB fusion protein (Jacobs, M., et al., (1991) *Mol. Gen. Genet.* 230:251–256). In this cassette, a Gram-positive ribosome binding site (RBS) was inserted upstream of luxA, with the luxB gene cloned in frame downstream of luxA. Although this approach has been successful in generating a number of novel genera of bioluminescent Gram-positive bacteria useful for certain environmental and food safety studies (e.g., the assessment of food products for contamination by such bacteria), these bacteria are not useful for studying pathogenicity. A major reason for this limitation is that the LuxAB fusion proteins described in the prior art are not stable at mammalian body temperatures, and are thus capable of catalyzing only minimal light production in bacterial cells at 37° C.

In fact, none of the bioluminescent Gram-positive bacteria which have been published to date produce enough light in vivo to make them useful for the in-vivo monitoring applications discussed above.

The present invention provides, inter alia, such methods, transposon cassettes, and other tools useful for generating bioluminescent bacteria, for example, Gram-positive bacteria and related organisms, suitable for studies relating to infection and/or pathogenesis.

SUMMARY OF THE INVENTION

In one aspect the present invention includes a transposon cassette for use in modifying a genome of a target organism. The target organism can be, for example, a gram-positive bacterium. In one embodiment, the transposon cassette comprises a polynucleotide sequence comprising first and second transposon inverted repeat sequences flanking an internal polynucleotide sequence, wherein the internal polynucleotide sequence comprises a first sequence of interest encoding polypeptide sequences present in a first orientation. The first sequence of interest typically lacks control sequences capable of promoting transcription in the target organism. Additionally, in certain embodiments, polynucleotide sequences derived from the transposon (e.g., IS or inverted repeat sequences) are obtained from a transposon derived from a gram-positive bacterium, for example, Tn4001 or Tn917. The transposon cassette may further comprise transposase encoding sequences, wherein the transposase is capable of inducing transposition mediated by the transposon inverted repeat sequences.

The transposon cassette of the present invention can be used to modify the genomes of a variety of microorganisms including, but not limited to Gram-positive bacteria (e.g., *Staphylococus* spp, *Streptococcus* spp., *Enterococcus* spp., *Bacillus* spp., *Clostridium* spp., *Mycobacterium* spp., *Corynebacterium* spp., *Listeria* spp., *Propriobacterium* spp., *Micrococcus* spp, *Lactobacillus* pp., and *Lactococcus* spp.); Gram-negative bacteria (e.g., *Vibrio* spp., *Brucella* spp., *Bordetella* spp., *Campylobacter* spp., *Pseudomonas* spp., *Escherichia* spp., *Enterobacter* spp., *Klebsiella* spp., *Serratia* spp., *Citrobacter* spp., *Proteus* spp., *Salmonella* spp., *Shigella* spp., and *Yersinia* spp); or other microorganisms (e.g., *Rickettsia* spp., *Rochalimaea* spp., *Coxiella* spp., *Treponema* spp., *Mycoplasma* spp., and *Chlamydia* spp.).

In one embodiment of the transposon cassette of the present invention, the first sequence of interest comprises at least one polynucleotide sequence encoding light generating polypeptide sequences. Such light generating polypeptide encoding sequences include, but are not limited to lux and/or luc genes, for example, (a) a polynucleotide encoding luxA, and luxB gene products; (b) a polynucleotide encoding luxA, luxB, luxC, luxD and luxE gene products; (c) a polynucleotide encoding luxY gene product; and (d) a polynucleotide encoding luc gene product. The first sequence of interest may further comprise at least one Gram-positive ribosome binding site sequence. For example, the polynucleotide sequence encoding light generating polypeptide sequences may encode luxA and luxB gene products. Further, in one embodiment the polynucleotide sequence encoding light generating polypeptide sequences may also comprise at least one Gram-positive ribosome binding site sequence upstream of at least one of the polynucleotide sequences encoding each of the luxA and luxB gene products. In another embodiment, the polynucleotide sequence encoding light generating polypeptide sequences further comprises a polynucleotide encoding luxC, luxD, and luxE gene products, which may also include at least one Gram-positive ribosome binding site sequence upstream of at least one, several, or all of the polynucleotide sequences encoding each of the luxA, luxB, luxC, luxD and luxE gene products. In still a further embodiment, the polynucleotide sequence encoding light generating polypeptide sequences further comprises a polynucleotide sequence encoding the luxY gene product, which may include at least one Gram-positive ribosome binding site sequence upstream of the luxY gene product.

The transposon cassette of the present invention may further comprise at least one coding sequence for a selectable marker. In one embodiment the selectable marker encodes a polypeptide conferring antibiotic resistance. Exemplary antibiotics that may be used for selection include, but are not limited to actinomycin, ampicillin, chloramphenicol, erythromycin, gentamycin sulfate, hygromycin, kanamycin, neomycin, penicillin, polymixin B sulfate and streptomycin sulfate. Sequences encoding polypeptides which confer antibiotic resistance may further comprises at least one Gram-positive ribosome binding site sequence upstream the coding sequence for the selectable marker.

In one embodiment of the transposon cassette of the present invention, the first sequence of interest comprises the following: (a) a polynucleotide sequence encoding light generating polypeptide sequences comprising a polynucleotide encoding luxA, luxB, luxC, luxD and luxE gene products, and further comprising at least one Gram-positive ribosome binding site sequence upstream of each of the polynucleotide sequences encoding each of the luxA, luxB, luxC, luxD and luxE gene products; and, (b) a coding sequence for a selectable marker encoding a polypeptide conferring kanamycin resistance.

In another aspect of the transposon cassette of the present invention, the internal polynucleotide sequence further comprises a transposase coding sequence operably linked to a promoter functional in the target organism. The transposase is capable of inducing transposition mediated by the transposon inverted repeats. Typically, the transposase coding sequence is in a second orientation relative to polypeptide coding sequences of the first sequence of interest encoding polypeptide sequences. Transcription termination sequences may be included at one of both ends of the transposase coding sequences. For example, at least one transcription termination control sequence may be interposed between the first sequence of interest encoding polypeptide sequences and the transposase coding sequence which is operably linked to a promoter functional in the target organism.

Exemplary first and second transposon inverted repeat sequences can be derived from Tn4001. A corresponding transposase coding sequence may also be derived from Tn4001.

The present invention further includes a vector comprising, (a) a vector backbone and (b) a transposon cassette of the present invention as described, for example, above. The transposase which facilitates transposition may typically be included within the transposon cassette, or alternately, may be provided on the vector backbone. The transposase coding sequence is operably linked to a promoter functional in the target organism. In preferred embodiments this promoter does not affect transcription of any coding sequences in the transposon cassette.

The vector backbone may further comprise at least one origin of replication that is functional in at least one target host cell, including, but not limited to, a Gram-positive origin of replication, a Gram-negative origin of replication, and/or an origin of replication that is functional in more than one type of target host cell. Such origins of replication may be wild-type or conditional (e.g., temperature-sensitive). Vector backbones comprising, for example, a Gram-positive and a Gram-negative origin of replication are useful for shuttling vector constructs between different types of microorganisms.

The vector backbone may further comprise a selectable marker sequence of interest operably linked to a promoter functional in a target organism, wherein the promoter does not affect transcription of any coding sequences in the transposon cassette. Such a selectable marker coding sequence may, for example, encode a polypeptide conferring antibiotic resistance. Useful selection antibiotics include, but are not limited to actinomycin, ampicillin, chloramphenicol, erythromycin, gentamycin sulfate, hygromycin, kanamycin, neomycin, penicillin, polymixin B sulfate and streptomycin sulfate.

Alternatively, or in addition to a selectable marker coding sequence, the vector backbone may comprises at least one polynucleotide sequence encoding light generating polypeptide sequences operably linked to a promoter functional in a target organism of interest, wherein the promoter does not affect transcription of any coding sequences in the transposon cassette. Such light generating polypeptide encoding sequences may be used, for example, to directly screen for microorganisms transformed by vectors of the present invention. In another aspect, the present invention includes the use of such polynucleotide sequence encoding light generating polypeptide sequences in any vector backbone to allow screening of transformed microorganisms for the presence of the vector carrying such sequences. In yet a further embodiment, the transposon cassette contains a polynucleotide sequence encoding a first light generating polypeptide sequences wherein the light generating first polypeptide produced from coding sequences within the transposon cassette produce bioluminescence of a characteristic first wavelength. The backbone vector may then comprise a polynucleotide sequence encoding a light generating second polypeptide sequences, wherein the second light generating polypeptide produces a characteristic second wavelength of bioluminescence that is detectably different from the first light generating polypeptide encoded by the transposon cassette. Various exemplary light generating polypeptide sequences have been discussed above and are further discussed hereinbelow.

Exemplary vector backbones include, but are not limited to, pAUL-A, pE194, and pSK. The backbone vectors of the present invention may comprise at least one transcription termination sequence in the vector backbone adjacent the transposon cassette, such that the transcription termination sequence essentially prevents transcription originating from any promoter present in the vector from reading through into the transposon cassette sequences. In another embodiment, the backbone vector may comprise two transcription termination sequences in the vector backbone wherein the transcription termination sequences flank the transposon cassette, such that the transcription termination sequences essentially prevent read-through transcription originating from any promoter present in the vector into the transposon cassette sequences.

Yet another aspect of the present invention includes a method for modifying a microorganism having a genome. In this method, the microorganism is transformed with any of the vectors of the present invention. The method may also include the step of culturing the transformed microorganism under conditions that facilitate transposition of the transposon cassette from the vector into the genome of the microorganism. Accordingly, the present invention also includes a cell carrying any of the vectors of the present invention, a cell produced by any of the methods of the present invention, as well as a modified host-cell carrying at least one transposon cassette of transposon cassettes of the present invention wherein expression of the first sequence within the transposon cassette is mediated by a transcriptional promoter endogenous to the target organism. Such cells may include, but are not limited to Gram-negative bacteria (e.g., *Vibrio* spp., *Brucella* spp., *Bordetella* spp., *Campylobacter* spp., *Pseudomonas* spp., *Escherichia* spp., *Enterobacter* spp., *Klebsiella* spp., *Serratia* spp., *Citrobacter* spp., *Proteus* spp., *Salmonella* spp., *Shigella* spp., and *Yersinia* spp.; Gram-positive bacteria (e.g., *Staphylococus* spp, *Streptococcus* spp., *Enterococcus* spp., *Bacillus* spp., *Clostridium* spp., *Mycobacterium* spp., *Corynebacterium* spp., *Listeria* spp., *Propriobacterium* spp., *Micrococcus* spp, *Lactobacillus* pp., and *Lactococcus* spp.; as well as other microorganisms (e.g., *Rickettsia* spp., *Rochalimaea* spp., *Coxiella* spp., *Treponema* spp., *Mycoplasma* spp., and *Chlamydia* spp.). Cells modified by the methods and compositions of the present invention may, for example, exhibit constitutive, inducible, and/or repressible bioluminescence. In one embodiment, the modified cell may exhibit bioluminescence upon infecting an animal susceptible to infection by the cell.

One method of the present invention is directed to a method of isolating cells capable of exhibiting bioluminescence. In this method, a target cell of choice (e.g., a selected microorganism such as a gram-positive bacteria) is transformed with a vector of the present invention. Such a vector may, for example, comprise, (i) a vector backbone compatible with the cell, and (ii) a transposon cassette as described herein, wherein the transposon cassette comprises a first sequence of interest encoding light generating polypeptide sequences lacking control sequences capable of promoting transcription in the target cell. The transformed cells are cultured under conditions permitting transposition of the transposon cassette. Transformed cells are then optically detected as cells (or colonies of cells) exhibiting bioluminescence. The cells exhibiting bioluminescence are then physically isolated and clonal isolates may be obtained (i.e., individual cells that have grown to form colonies).

The present invention further includes another method of isolating cells capable of exhibiting bioluminescence. In this method the cells of interest (e.g., a microorganism) are transformed with a vector comprising, (i) a vector backbone compatible with the cell, wherein the vector backbone comprises a polynucleotide encoding light generating polypeptide sequences operably linked to a promoter functional in the cells, wherein the light generating polypeptide produces bioluminescence of a characteristic first wavelength, and (ii) a transposon cassette of the present invention. The transposon cassette may include a polynucleotide sequence comprising first and second transposon inverted repeat sequences flanking an internal polynucleotide sequence, wherein the internal polynucleotide sequence comprises a first sequence of interest encoding light generating polypeptide sequences present in a first orientation the light generating polypeptide producing bioluminescence of a characteristic second wavelength. In such transposon cassettes the first sequence of interest lacks control sequences capable of promoting transcription in the target organism. The internal polynucleotide sequence may further comprise a transposase coding sequence operably linked to a promoter functional in the target organism. The transposase being capable of inducing transposition mediated by the transposon inverted repeats. In one embodiment the transposase coding sequence is in a second orientation relative to polypeptide coding sequences of the first sequence of interest encoding polypeptide sequences. Alternatively, one or more transcription termination sequences may be placed adjacent the transposase, and/or the transposase may be on the vector backbone instead of within the transposon cassette. Transformed cells are identified by their ability to produce bioluminescence of the characteristic first wavelength. The transformed cells are cultured under conditions permitting transposition of the transposon cassette. Transposants are optically detected, i.e., they are capable of producing bioluminescence of the characteristic second wavelength. These bioluminescent cells and/or colonies, which bioluminesce at the characteristic second wavelength, are isolated (e.g., by physical manipulation).

The present invention also includes methods of identifying active host-cell gene promoters. In this method, the host-cell of interest is transformed with a vector of the present invention carrying a transposon cassette of the present invention. The transformed cells are cultured under conditions permitting transposition of the transposon cassette. These transformed host-cells are then screened for expression of the first sequence of interest encoding polypeptide sequences. The active host-cell gene promoter mediating expression of the first sequence of interest encoding polypeptide sequences is then identified. Another method of identifying active host-cell gene promoters infecting a first animal with a microorganism carrying a vector of the present invention. The vector may, for example, comprise (a) a vector backbone compatible with the microorganism, and (b) a transposon cassette comprising a polynucleotide sequence comprising first and second transposon inverted repeat sequences flanking an internal polynucleotide sequence, wherein the internal polynucleotide sequence comprises a first sequence of interest encoding (i) light generating polypeptide sequences present in a first orientation, and (ii) a polypeptide sequence conferring antibiotic resistance, the first sequence of interest lacking control sequences capable of promoting transcription in the target organism. In one embodiment, the internal polynucleotide sequence further comprises a transposase coding sequence operably linked to a promoter functional in the target organism, where the transposase is capable of inducing transposition mediated by the transposon inverted repeats. The transposase coding sequence may be in a second orientation relative to polypeptide coding sequences of the first sequence of interest. Alternatively, or in addition, at least one transcription termination sequence may be placed adjacent the tranposase coding sequence. In yet another embodiment, the transposase may be placed on the vector backbone instead of within the transposon cassette. In the method, host-cells are selected, in the animal, for antibiotic resistant transposants. The antibiotic resistant transposants are isolated from the animal. These transposants are then screened in vitro to identify transposants that do not exhibit constitutive bioluminescence. Such transposants are then used to infect a second animal and are screened for their ability to exhibit bioluminescence in vivo upon infection of the second animal. Transposants exhibiting bioluminescence in vivo upon infection of the second animal are then isolated. The active gene promoter associated with the first sequence of interest in the transposants exhibiting bioluminescence in vivo upon infection of the second animal is then identified, for example, by sequencing genomic DNA adjacent the transposon cassette sequences. Alternatively, the transposants exhibiting bioluminescence in vivo upon infection of the second animal are isolated and used to infect third and fourth animals. The infected third animal may be treated with a compound of interest. The treated, infected third animal and the untreated, infected fourth animal are then monitored for bioluminescence in vivo. Bioluminescence from the third and fourth animals are then compared to determine whether the compound of interest detectably affects in vivo bioluminescence in the third animal relative to the fourth, wherein reducing or eliminating in vivo bioluminescence in the third animal relative to the fourth indicates pharmacological effectiveness against the microorganism of interest in the animal.

A further aspect of the present invention includes a method of monitoring the proliferation of a microorganism of interest in a medium of interest. In this method a microorganism of interest is transformed with a vector of the present invention, comprising a transposon cassette of the present invention. The transposon cassette typically includes a first sequence of interest encoding light generating polypeptide sequences lacking control sequences capable of promoting transcription in the target organism. As described above, the transposase may be contained within the transposon cassette or on the vector backbone. The transformed microorganisms are cultured under conditions permitting transposition and screened for transposants capable of exhibiting bioluminescence. The medium of interest is inoculated with bioluminescent transposants. The medium is then sampled and the samples monitored for the degree of bioluminescence over time, wherein an increase in the degree of bioluminescence over time is correlated to proliferation of the microorganism in the sample. The method may further comprise adding a compound of interest to the medium, and evaluating the effect of the compound on proliferation of the microorganisms.

These and other embodiments of the present invention will readily occur to those of ordinary skill in the art in view of the disclosure herein.

DETAILED DESCRIPTION OF THE INVENTION

Figure 1:
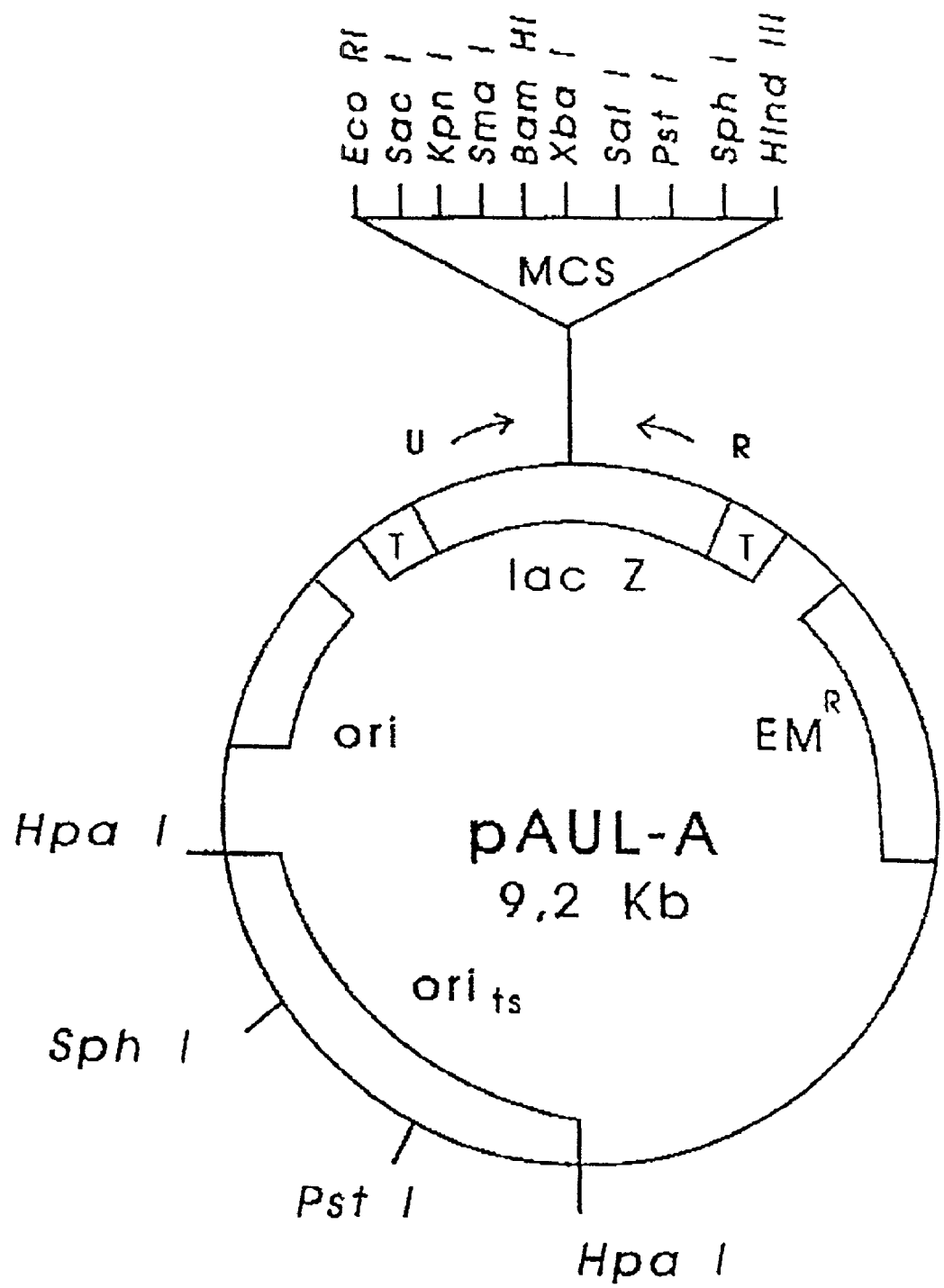
FIG. 1 presents a schematic diagram of the pAUL-A backbone vector.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); *Methods In Enzymology* (S. Colowick and N. Kaplan, eds., Academic Press, Inc.); and *Handbook of Experimental Immunology,* Vols. I–IV (D. M. Weir and C. C. Blackwell, eds., 1986, Blackwell Scientific Publications); Ausubel, F. M., et al., *Current Protocols in Molecular Biology,* John Wiley and Sons, Inc., Media, Pa. (1995). Sambrook, J., et al., *Molecular Cloning: A Laboratory Manual,* Second Edition, Cold Spring Harbor Laboratory (Cold Spring Harbor, N.Y.) (1989)).

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

Definitions

In describing the present invention, the following terms will be employed, and are intended to be defined as indicated below. Unless otherwise indicated, all terms used herein have the same meaning as they would to one skilled in the art of the present invention.

As used in this specification and the appended claims, the singular forms "a," "an" and "the" include plural references unless the content clearly dictates otherwise. Thus, for example, reference to "an antigen" includes a mixture of two or more such agents.

The terms "nucleic acid molecule" and "polynucleotide" are used interchangeably to and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral, eucaryotic, or procaryotic DNA, and even synthetic DNA sequences. A transcription termination sequence may be located 3' to the coding sequence.

Typical "control elements", include, but are not limited to, transcription regulators, such as promoters, transcription enhancer elements, transcription termination signals, and polyadenylation sequences; and translation regulators, such as sequences for optimization of initiation of translation, e.g., Shine-Dalgarno (ribosome binding site) sequences, and translation termination sequences. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

A double-stranded DNA molecule comprises two strands of DNA having "opposite orientations," one strand being designated 5' to 3'; the second strand being its complement. Thus, a first coding sequence in a first strand and a second coding sequence in the complementary strand have "opposite" orientations relative to each other, that is, the first and second coding sequences are in opposite orientations relative to each other.

An "isolated polynucleotide" molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein.

"Operably linked" refers to an arrangement of elements wherein the components so described are configured so as to perform their usual function. Thus, a given promoter that is operably linked to a coding sequence (e.g., a reporter gene) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transformed. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington., D.C., USA, and normalized by Gribskov, *Nucl. Acids Res.* 14(6):6745–6763 (1986). An exemplary implementation of this algorithm to determine percent identity of a sequence is provided by the Genetics Computer Group (Madison, Wis.) in the "BestFit" utility application. The default parameters for this method are described in the *Wisconsin Sequence Analysis Package ProGram Manual*, Version 8 (1995) (available from Genetics Computer Group, Madison, Wis.). A preferred method of establishing percent identity in the context of the present invention is to use the MPSRCH package of proGrams copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable proGrams for calculating the percent identity or similarity between sequences is generally known in the art, for example, another alignment proGram is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these proGrams can be found on the internet.

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%–85%, preferably at least about 90%, and most preferably at least about 95%–98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "gene" refers to a polynucleotide containing at least one open reading frame that is capable of encoding a particular product (e.g., a polypeptide, protein or RNA). Typically, the term "gene" includes control sequences associated with the expression of the product. Any of the polynucleotide sequences described herein may be used to identify larger fragments or full-length coding sequences of the genes with which they are associated. Methods of isolating larger fragment sequences are known to those of skill in the art.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10–14 nucleotides in length having at least approximately 70% sequence identity with the sequence of the selected nucleic acid probe. Stringent hybridization conditions typically allow detection of target nucleic acid sequences of at least about 10–14 nucleotides in length having a sequence identity of greater than about 90–95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with an polypeptide encoded by the sequence.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "vector" is capable of transferring gene sequences to target cells (e.g., viral vectors, non-viral vectors, particulate carriers, and liposomes). Typically, a "vector construct" refers to a nucleic acid vector capable of transferring sequences of interest into target cells. Nucleic acid vectors can be transiently present in or capable of replication in target cells. Transient vectors typically do not have an origin of replication that can function in the target cell, or one which does not function under certain conditions in the target cell (a "conditional" origin of replication).

"Nucleic acid expression vector" refers to an assembly which is capable of directing the expression of a sequence or gene of interest. The nucleic acid expression vector includes a promoter which is operably linked to the sequences or gene(s) of interest. Other control elements may be present as well. For example, in addition to the components of an expression cassette, the plasmid construct may also include one or more bacterial origin(s) of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

An "expression cassette" comprises any nucleic acid construct which contains polynucleotide gene(s) or sequence(s) capable of being expressed in a cell. Expression cassettes may contain, in addition to polynucleotide gene(s) or sequence(s) of interest, additional transcriptional, translational or other regulatory or control elements. Such cassettes are typically constructed into a "vector," "vector construct," or "expression vector," (i.e., a "nucleic acid expression vector) in order to transfer the expression cassette into target cells. In the context of the present invention, an expression cassette typically has no transcriptional promoter, but does have translation enhancing sequences, such as Shine-Dalgarno sequences.

A "transposon" as used herein defines a polynucleotide which comprises a repeated element capable of relocating from one genetic locus to another (e.g., from a chromosomal point to another chromosomal point, or from an episomal point to a chromosomal point), i.e., a transposon is a mobile genetic element. In a preferred embodiment of the present invention, a "transposon cassette" comprises a minimum unit required for transposition (e.g., first and second transposon inverted repeat sequences flanking an internal polynucleotide sequence comprising at least a transposase capable of inducing transposition mediated by said transposon inverted repeats). Alternately, a transposon cassette may be first and second transposon inverted repeat sequences flanking an internal polynucleotide sequence, where the transposase function is provided in trans or is encoded external to the transposon cassette (i.e., outside of the two transposon inverted repeats flanking the internal polynucleotide sequence). As used herein, a transposon cassette comprises at least two inverted repeat sequences flanking an internal region. The internal region may contain transposase coding sequence and/or other sequences of interest. A schematic representation of a transposon cassette is as follows: IR-internal region-IR, where IR represents the inverted repeats. In another embodiment, a representation is as follows: IR-tnp-IR, where tnp represents a transposase gene. Further, IR—sequence of interest—tnp-IR represents yet another embodiment, capable of inducing transposition mediated by the IR sequences. Further sequences, 5' and 3' of the inverted repeats may be included in the transposon cassette where indicated. A transposon cassette that is "functional" in a host organism is one that is capable of undergoing transposition in that organism. The term "transposant" typically refers to a cell in which a transposon has integrated into the cell's genome. Further, the term "gram-positive transposon" refers to a transposable element derived from a gram-positive bacteria, for example transposons Tn4001 and Tn917.

"Gram-positive" is a taxonomic feature referring to bacteria which resist decolorization with any standard Gram-staining dyes. In contrast, Gram-negative bacteria are easily decolorized with certain organic solvents such as ethanol or acetone. The ability of bacteria to retain or resist staining generally reflects the structure of the cell wall and it has been suggested that Gram-negative bacteria have more extensive peptidoglycan crosslinking and less permeable cells walls than their Gram-negative counterparts. Non-limiting examples of Gram-positive bacteria include: *Stapholococcus, Streptococcus*, certain *Bacillus, Anthrax, Mycobacterium*, etc.

"Light-generating" is defined as capable of generating light through a chemical reaction or through the absorption of radiation.

"Light" is defined herein, unless stated otherwise, as electromagnetic radiation having a wavelength of between about 300 nm and about 1100 nm.

"Visible light" is defined herein, unless stated otherwise, as electromagnetic radiation having a wavelength of between about 400 nm and about 750 nm.

"Light-generating protein" is defined as a protein or polypeptide capable of generating light through a chemical reaction (e.g., bioluminescence, as generated by luciferase) or through the absorption of radiation (e.g., fluorescence, as generated by Green Fluorescent Protein).

"Luciferase," unless stated otherwise, includes prokaryotic and eukaryotic luciferases, as well as variants possessing varied or altered optical properties, such as luciferases that produce different colors of light (e.g., Kajiyama, N., and Nakano, E., (1991) *Protein Engineering* 4(6):691–693. "Lux" refers to prokaryotic genes associated with luciferase and photon emission. "Luc" refers to eukaryotic genes associated with luciferase and photon emission.

"Animal" as used herein typically refers to a non-human animal, including, without limitation, farm animals such as cattle, sheep, pigs, goats and horses; domestic animals such as dogs and cats; laboratory animals including rodents such as mice, rats and guinea pigs; rabbits; birds, including domestic, wild and game birds such as chickens, turkeys and other gallinaceous birds, ducks, geese, and the like. The term does not denote a particular age. Thus, adult, newborn individuals, and fetuses are intended to be covered.

"Analyte" as used herein refers to any compound or substance whose effects (e.g., induction or repression of a specific promoter) can be evaluated using the test animals and methods of the present invention. Such analytes include, but are not limited to, chemical compounds, pharmaceutical compounds, polypeptides, peptides, polynucleotides, and polynucleotide analogs. Many organizations (e.g., the National Institutes of Health, pharmaceutical and chemical corporations) have large libraries of chemical or biological compounds from natural or synthetic processes, or fermentation broths or extracts. Such compounds/analytes can be employed in the practice of the present invention.

Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

General Overview of the Invention

As discussed above, the synthesis of light in naturally occurring bioluminescent bacteria is encoded by five genes. In one embodiment, these genes are clustered in an operon (luxCDABE) that can be moved into non-bioluminescent bacteria to produce a bioluminescent phenotype. To date, all identified species of naturally occurring marine and terrestrial bioluminescent bacteria are Gram-negative; the transformation of Gram-positive bacteria to a bioluminescent phenotype has been limited, due in part to the differing genetics of these two bacterial groups.

The constructs and methods of the present invention facilitate the ability to confer bioluminescence properties on a bacterium of one's choice, so that the bacterium could, for example, be followed with in vivo monitoring in various models of infection or used in the tracking of bacteria, e.g., in the food industries. In particular, it would be desirable to confer such bioluminescence properties on Gram positive bacteria, because many bacteria pathogenic to mammals are in fact Gram-positive. For example, infections caused by *Stapholococcus*, a Gram-positive cocci, are ubiquitous and include, e.g., abscesses, mastitis, pneumonia, bacteremia, osteomyletis, enterocolitis and toxic shock syndrome (TSS). Another Gram-positive cocci, *Streptococcus* is the primary cause of pharyngeal infections (strep throat). Gram-positive bacilli such as *Anthrax* and *Listeria* (which causes meningitis) can cause severe, and even fatal infections in humans and other mammals.

Further, it would also be desirable to confer bioluminescence properties on organisms such as *Chlamydia, Treponema pallidum, Heliobacter pylori*, and other organisms which are difficult to manipulate and which have not previously been amenable to pharmaceutical intervention.

The present invention teaches the use of transposon cassettes (e.g., Tn4001, Tn917, and others) to facilitate the genetic manipulation of microorganisms of interest, including, but not limited to, Gram-negative bacteria (including *Heliobacter pylori* and others) and Gram-positive bacteria (including related organisms such as *Chlamydia* and *Treponema pallidum*).

In one aspect, the present invention relates to the re-engineering of the entire *Photorhabdus luminescens* lux operon to first remove the endogenous promoter sequences associated with the lux operon genes, and finally introduce Gram-positive control elements immediately upstream of each of the lux operon genes, in particular, Shine-Dalgarno sequences (i.e., ribosome binding sites). The luciferase enzyme is encoded by luxA and luxB, whereas the enzymes responsible for the aldehyde biosynthesis are encoded by the three genes luxC, luxD and luxE. However, since aldehyde can rapidly diffuse across cellular membranes and is commercially available (e.g., Sigma), the genes encoding the synthesis of this substrate (luxCDE) are not an absolute necessity for bioluminescence and can be substituted by the addition of this compound, or a suitable luciferin, exogenously. In order to generate a bioluminescent Gram-positive bacterium therefore, it is only necessary to ensure that the cell can synthesize a functional luciferase.

In one embodiment of the present invention, a novel promoterless luxABCDE cassette was further modified by addition of a promoterless kanamycin resistance gene immediately adjacent to the 3' end of the coding strand of the operon. While the use of kanamycin as a selectable marker is explicitly described herein, the use of other selectable marker sequences appropriate to the target host cell are also contemplated and may be used in the practice of the present invention. For example, in the case of a Gram-positive target host, genes useful for conferring antibiotic resistance to the following antibiotics are non-limiting examples of those that may be used: actinomycin, ampicillin, chloramphenicol, erythromycin; gentamicin sulfate; hygromycin, neomycin, penicillin, polymixin B sulfate and stretomycin sulfate.

Transformation of organisms of interest to a bioluminescent phenotype was then accomplished by integrating the cassette into the genome of those organisms by means of a transposon. The novel luxABCDE $km^R$ cassette was inserted into the Tn4001 transposon, and cells of interest were then transformed with a shuttle vector carrying the Tn4001 luxABCDE $km^R$ construct. Transposition events subsequent to transformation resulted in integration of the luxABCDE $km^R$ cassette into the genome of the host organism and resulted in the ability of the organism to bioluminesce; integration of the otherwise promoterless cassette behind an active promoter sequence yielded host organisms having a bioluminescent phenotype. The kanamycin resistance gene facilitated selection of those integrants. Using this approach several different genera of Gram-positive bacteria were made brightly bioluminescent, either constitutively or inducibly.

The present invention generally relates to transposon constructs comprising, a promoterless coding sequence of interest, e.g., a light-generating protein coding cassette. These transposon constructs can be inserted into a suitable backbone (e.g., a shuttle vector) and thereby confer the ability to produce the product of the coding sequence of interest (which, in the case of a light-generating protein, also confers the ability to produce light in a cell or animal) upon integration of the coding sequence of interest, (e.g., light-generating protein coding cassette) behind an active promoter region in the host cell genome. In one aspect of the present invention, the transposon cassettes described herein allow, for the first time, more than minimal amount of light to be produced from Gram-positive bacteria at physiological temperatures.

Selection of integrants is facilitated by further modification of the transposon cassette to include a promoterless selectable marker coding sequence downstream of the coding sequence of interest and operably linked thereto. In this case, to be operably linked, the selectable marker is typically located in close proximity to the coding sequence of interest and the open reading frame of the selectable marker is in the same 5' to 3' orientation as that of the coding sequence of interest.

In one embodiment, the light generating protein coding cassette contains promoterless bacterial lux genes recombinantly engineered to promote functional expression of lux for example, by arranging the genes in the order luxABCDE. Thus, this cassette rearranges the unmodified order of these genes, namely luxCABDE. By including both the structural genes (luxAB) and substrate-encoding genes (luxCDE), this coding cassette does not require the addition of exogenous substrate. Moreover, the rearrangement of genes together with the introduction of Gram-positive Shine-Dalgarno sequences confers a greater light-generating ability upon integration than the unmodified order. A Gram-positive Shine-Dalgarno sequence ("SD") is preferably inserted before (typically 5' to) one, more than one, or all of the lux genes coding sequences (e.g., SD-luxA-SD-luxB-SD-luxC-SD-luxD-SD-luxE).

Another cassette provided by the present invention includes polynucleotides encoding luxAB, but not including the substrate encoding genes. When employing such luxAB cassettes, exogenous substrate, for example, aldehyde, is provided to monitor the ability of transformed organisms to produce light. The luxAB coding cassettes typically include a DNA sequence which enhances translation between the genes encoding for luxA and luxB (for example, Gram-positive Shine-Dalgarno sequences).

Yet another light generating protein coding cassette of the present invention includes polynucleotides encoding functional luc, an eukaryotic luciferase gene. In one embodiment, the coding cassette includes polynucleotides encoding luc and control elements, such as Shine-Dalgarno sequences, for example, from Gram-positive bacteria.

In another aspect, the transposon cassettes described herein may be introduced into a plasmid or vector, e.g., various shuttle vector backbones. Also provided are methods of modifying Gram-positive organisms to a bioluminescent phenotype using those shuttle vector constructs. Target host cells are transformed with shuttle vector DNA to provide the opportunity for a transposition of the transposon cassette; subsequent integration of the transposon cassette downstream of an active promoter region in the host cell genome gives rise to a bioluminescent phenotype, which may be constitutive, inducible or repressible depending on the properties of the promoter region behind which the transposon cassette has integrated.

In another aspect of the present invention, the bioluminescent transposants are themselves useful in a number of applications. For example, pathogenic transposants can be used to study the promoters active during pathogenesis. In one embodiment, experimental animals are infected with pathogenic bacteria transformed with a transposon cassette of the present invention (e.g, using pAUL-ATn4001 luxAB-CDE km$^R$ shuttle vector construct), and a selection is applied to select for transposants. After extraction and culturing of cells to select for non-constitutive, bioluminescent colonies, cells from those colonies are re-injected into other experimental animals, where induction of light production in vivo, for example during the initial stages of infection, indicates a bacterial promoter turned on in response to infection of the host animal.

Further, the promoter sequences which mediate bioluminescence in a transposant may be identified. For example, bacteria are isolated from experimental animals that exhibit bioluminescence attributable to the activity of promoters induced by infection. The promoters are then isolated by, for example, inverse PCR amplification using primers based on known gene sequences adjacent or in close proximity to the active bacterial promoters, for example, gene sequences present in the coding sequence of interest, such as, one of the lux genes or kanamycin resistance sequence of the integrated transposon cassette. The amplification products are then sequenced by methods known in the art. Alternately, chromosomal DNA may be directly isolated from a single bacterial colony of interest, and then sequenced using primers based on gene sequences adjacent or in close proximity to the active bacterial promoters.

Still further, colonies that exhibit bioluminescence attributable to the activity of promoters induced by infection can be used to identify effective pharmaceutical agents. For example, transposant cells which exhibit bioluminescence attributable to the activity of promoters induced by infection are used to infect experimental and control animals. The experimental animals are then treated with a pharmaceutical agent of interest. Both the experimental animals and the controls are monitored for bioluminescence, and effective agents identified as those which extinguish bioluminescence.

In yet another aspect, transposants may be used as a means of monitoring bacterial growth in foodstuffs, and further as a means of identifying agents or conditions which suppress or encourage that growth.

Advantages of the present invention include, but are not limited to, (i) transforming a variety of organisms, including Gram-positive bacteria and organisms such as *Chlamydia*, *Treponema pallidum*, as well as Gram-negative and others to a bioluminescent phenotype; (ii) obtaining high levels of light generating protein expression in those transformed organisms, which, for example, permits more sensitive detection of bioluminescence both in vitro and in vivo; (iii) integration of the transposon cassette into the host chromosome such that the cassette becomes operably linked to host cell promoters, which, for example, permits identification of promoters involved in pathogenesis; and stable light production from such organsims at physiological temperatures (e.g., 37° C.–42° C.).

Specific aspects of the methods and constructs of the present invention are discussed below.

1. Gram-Positive Transposons Derived from Gram-Positive Bacteria

The practice of the present invention employs transposons derived from gram-positive bacteria, including but not limited to, transposons Tn4001, Tn917, Tn5401 and Tn5706, as well as sequences comprising such transposons, including, but not limited to IS sequences and transposase encoding sequences. In preferred embodiments, Tn4001 is employed. Tn4001, a class I composite-type transposon originally isolated from *Staphyloccus aureus* (GeneBank Accession No. M18086, base pair 1–1,324 of the sequence; see Byrne, M. E., Rouch, D. A., and Skurray, R. A. (1989) *Gene* 81:361–367). This element is capable of inserting with a high degree of randomness into the bacterial chromosome of Gram-positive organisms. Experiments performed in support of the present invention indicate that the transposon functions in Gram-negative host cells as well.

The components of the Tn4001 transposon include (1) two identical copies of the IS256 insertion sequence, present as inverted repeats (IR's) which define an insertion sequence therebetween, and (2) a transposase gene located within the inverted repeats, which defines an insertion. Alternately, the transposon may include sequences outside of the IR regions downstream of the 3' IR region. Generally, when referring to the transposon the inverted repeats are considered to be the boundary of a functional transposon unit. This basic structure may be further modified and placed into a variety of vector backbones, as discussed below.

For example, additional sequences of interest may be inserted between the inverted repeats (e.g., 5'-IR—sequence of interest—IR 3'); alternately, they may be inserted following the 3'-IR sequence. Typically, the additional sequences of interest lack an associated promoter region. Further, the additional sequences of interest are preferably introduced into the Tn4001 transposon such that the direction of transcription for the inserted sequences is opposite that of the direction of the transposase coding sequence, and is therefore not under influence of transposase promoter. Hence, the sequences will not be transcribed unless and until integration of the insertion sequence behind an active or activatable promoter region occurs. As a corollary, this means that the coding sequences for the open reading frames for the sequences of interest and the transposase are in opposite orientations in the DNA.

Alternately, the tranposase sequence may be present in the same orientation as the sequence of interest, provided that it is located downstream of that sequence, in order to avoid read-through from the endogenous transposase promoter and expression of the light generating protein gene product prior to integration.

For example, polynucleotide sequences encoding a light generating protein, which proteins are discussed below, may be inserted between the inverted repeats. When used in the practice of the present invention, the light-generating protein sequences are typically employed in the absence of a promoter contained within the tranposable element. That is, no promoter sequence is typically present within the transposon that can mediate transcription of the light-generating protein. In a preferred embodiment, the light-generating protein sequence is inserted adjacent or in close proximity to the 3' end of the 5' inverted repeat sequence, e.g., 5'-IR-light generating sequences ... —IR-3'. Further, the sequence is inserted in an orientation opposite that of the tranposase sequence, such that even with transcription of the transpose sequence there is no transcription of the sequence of interest (e.g., light-generating polypeptide coding sequences) prior to integration into the genome of an organism of interest adjacent an active host promoter region.

The transposon may be further modified by inserting polynucleotide sequences which code for one or more selective markers between the IR sequences. The marker employed is chosen to be functional in the target organism of interest, and serves to identify candidate transposition events where expression of the selectable marker protein is related to transposition events of interest. As described for sequences encoding the light-generating polypeptide, transcription of the selectable marker is also in the opposite direction relative to transcription of the transposase sequences. Accordingly, there is no transcription of the selectable marker prior to integration into the genome of an organism of interest adjacent an active host promoter region.

For example, an antibiotic resistance genes may be employed as a selective marker. In one embodiment of the present invention, a promoter-less kanamycin resistance gene is employed as a selective marker in the practice of the present invention.

In a particularly preferred embodiment of the invention, a promoterless nucleotide sequence encoding kanamycin resistance is inserted downstream of, and is operably linked to, the light-generating protein genes. The $km^R$ sequence is inserted, either immediately adjacent to the 3' end of the sequence encoding a light generating protein or in close proximity thereto with the light-generating protein coding sequence, for example, 5'-IR-light generating polypeptide-km ... —IR-3'. This configuration provides a means for the selection of cells wherein the transposable element has integrated into the bacterial chromosome, as well as a means for distinguishing among integrants located adjacent to either constitutively- or nonconstitutively-active promoters, as will be discussed below.

Alternately, other sequences of interest may be inserted outside of the inverted repeats. In particular, a sequence of interest may be inserted downstream of the 3' inverted repeat sequence. For example, in one embodiment of the present invention, the transposase sequence can be moved outside of the transposable element defined between the IR regions, and placed downstream of the 3'-IR sequence on a vector backbone.

2. Light-Generating Proteins

The practice of the present invention will typically employ nucleotide sequences encoding light generating proteins, and the property of bioluminescence which transcription of those sequences will confer.

Bioluminescence provides a powerful reporter system for studying bacterial infection (e.g., U.S. Pat. No. 5,650,135). Luciferase is a term applied to members of a family of diverse enzymes which share the property of producing light when provided with a substrate (e.g., luciferin, long-chain aldehyde or colentrazine), an energy source (e.g., ATP or $FMNH_2$) and oxygen. Luciferases can be broadly classified into eukaryotic luciferases and prokaryotic luciferases. Eukaryotic luciferase ("luc") is typically encoded by a single gene (see, e.g., de Wet, J. R., et al., (1985), *Proc. Natl. Acad. Sci. U.S.A.* 82:7870–7873; de Wet, J. R., et al., (1987) *Mol. Cell. Biol.* 7:725–737). An exemplary eukaryotic organism containing a luciferase system is the North American firefly *Photinus pyralis*. Firefly luciferase has been extensively studied, and is widely used in ATP assays. cDNAs encoding luciferases from *Pyrophorus plagiophthalamus,* another species of click beetle, have been cloned and expressed (Wood, K. V., et al. (1989) *Science* 244:700–702). This beetle is unusual in that different members of the species emit bioluminescence of different colors. Four classes of clones, having 95–99% homology with each other, were isolated. They emit light at 546 nm (green), 560 nm (yellow-green), 578 nm (yellow) and 593 nm (orange). The last class (593 nm) may be particularly advantageous for use as a light-generating moiety with the present invention, because the emitted light has a wavelength that penetrates tissues more easily than shorter wavelength light.

Bacterial luciferase ("lux") is typically made up of two subunits ($\alpha$ and $\beta$) encoded by two different genes (luxA and luxB) on the lux operon. Three other genes on the operon (lux C, lux D and luxE) encode the enzymes required for biosynthesis of the aldehyde substrate. Bacterial lux is present in certain bioluminescent Gram-negative bacteria (e.g., *Photorhabdus luminescens*) and the wild-type operon is ordered CDABE.

In addition, another bacterial gene, luxY, isolated from *Vibrio fischeri* strain Y-1, encodes a yellow fluorescent protein (YFP), a substrate which emits yellow light with a lambda max of 545 nm when acted upon by the luciferase enzyme. See Baldwin, T. O., et al. (1990) *Biochem* 29:5509–5515.

A variety of luciferase encoding genes have been identified including, but not limited to, the following: B. A. Sherf and K. V. Wood, U.S. Pat. No. 5,670,356, Kazami, J., et al., U.S. Pat. No. 5,604,123, S. Zenno, et al. U.S. Pat. No. 5,618,722; K. V. Wood, U.S. Pat. No. 5,650,289, K. V.

Wood, U.S. Pat. No. 5,641,641, N. Kajiyama and E. Nakano, U.S. Pat. No. 5,229,285, M. J. Cormier and W. W. Lorenz, U.S. Pat. No. 5,292,658, M. J. Cormier and W. W. Lorenz, U.S. Pat. No. 5,418,155, de Wet, J. R., et al. (1987) *Molec. Cell. Biol.* 7:725–737; Tatsumi, H. N., et al. (1992) *Biochim. Biophys. Acta* 1131:161–165 and Wood, K. V., et al. (1989) *Science* 244:700–702, all herein incorporated by reference.

2A. Lux-Encoding Gene Cassettes

In one aspect of the invention, gene cassettes comprising polynucleotides encoding both the structural and substrate-encoding lux gene-products are provided. Experiments performed in support of the present invention have demonstrated that rearranging the lax genes, for example, from the wild-type CABDE to ABCDE, and inserting Gram-positive Shine-Dalgarno sequences before one or more of the lux genes, confers on the resulting luciferase an enhanced ability to produce light. Suitable Gram-positive Shine-Dalgarno sequences (e.g., Example 1, Table 1) will be known to those of skill in the art in view of the teachings of the specification, and are also described in the Examples below. The luxAB-CDE cassettes express not only luciferase, but also the biosynthetic enzymes necessary for the synthesis of the lux luciferase's substrate—aldehyde. Accordingly, oxygen is the only extrinsic requirement for bioluminescence when this expression cassette is used.

In another aspect of the invention, luxABCDEY cassettes are provided. Adding the luxY gene to the luxABCDE gene cassette results in broadening the range of wavelength of light emitted during bioluminescence towards the red end of the visible light spectrum. Given that longer-wavelength light more easily penetrates living tissue as compared to light of shorter wavelengths, selected embodiments of the luxABCDE gene cassette of the present invention will therefore additionally include the luxY coding sequence, as a means of increasing the sensitivity of applications which employ bioluminescence as a reporter means.

Experiments performed in support of the present invention demonstrate that the transposon constructs of the present invention confer the ability of bioluminescence in the organisms of interest only upon integration of the insertion sequence into the host cell genome behind an active promoter sequence. Those transposon constructs employ light generating polypeptide sequences, e.g., luxABCDE and luxABCDEY, that do not include an integral promoter. Thus, there will be no promoter sequence present to mediate transcription of the light-generating protein sequences present within the IR-defined transposable region. Bioluminescence is therefore dependent on integration.

In still another aspect, luxAB gene cassettes are provided. The luxAB cassettes typically contain a Gram positive ribosome binding site (also referred to as a "Shine-Dalgarno" sequence) operably linked upstream of each of the polynucleotides encoding luxA and B. Host organisms carrying the luxAB cassette exhibit bioluminescence when provided with exogenous aldehyde substrate. As described herein, these luxAB cassettes confer higher levels of luciferase activity than found in previously known constructs, particularly when expressed in Gram-positive bacteria such as *Stapholococcus* or *Streptococcus*.

2B. Luc-Encoding Expression Cassettes

The present invention also includes gene cassettes that allow for expression of eukaryotic luciferase. Typically, as for the lux gene cassettes discussed above, the luc expression cassette is employed in the absence of a promoter contained within the transposable region. The lux and luc genes can also be combined for use in the transposon cassette constructs of the present invention.

In one embodiment in which these cassettes are combined, one of the light-generating protein coding cassettes may be present in the vector backbone in place of an antibiotic resistance gene, and the other as a means of identifying active host cell promoters. For example, a vector construct may include both a promoterless luxAB coding cassette in the first sequence of interest of the transposon cassette, and a luc coding cassette operably linked to a promoter functional in the target organism on the vector. Organisms transformed with such a construct could then be identified upon supplying the luc substrate, upon which the transformed organisms would exhibit bioluminescence of a wavelength characteristic of the luc gene product; transposants in which the luxAB cassette has successfully integrated behind an active promoter may then be identified by the bioluminescence exhibited upon supplying aldehyde. Alternately, the luxABCDE coding cassette may be used in the transposon construct and the luxABCDEY coding cassette on the vector backbone, obviating the need for addition of an exogenous substrate while maintaining the ability to discern the source of the light being produced based on the emitted wavelength.

In alternative embodiments, the sequences producing two or more light-generating polypeptides producing emitted light at two or more wavelengths may be provided as the first sequence of interest in separate transposon cassettes; the transposon cassettes may in turn be provided in either a single vector backbone or in multiple vector backbones. Such constructs may be used to produce, for example, single microorganisms bearing multiple transposon cassettes of the present invention, where the transposon cassettes may each encode light generating polypeptides that emit light at different wavelengths.

3. Selection Markers

As stated above, the practice of the present invention may employ selectable markers, both as a component of the Tn4001 transposon cassette, as discussed above, and as an element of the vector backbone, as discussed below. A variety of selectable markers may be used; with the choice of which marker to employ being made on the basis of whether it is functional in the target organism of interest. When a selectable marker is used in the transposon cassette it does not have a transcriptional promoter operably linked to it. This allows for selection of transposons that have integrated adjacent operative promoters in the host cell genome. However, when a selectable marker is used in a backbone vector carrying a transposon cassette, such a selectable marker is typically operably linked to a functional transcriptional promoter in order to allow selection for the presence and/or absence of the vector. In a preferred embodiment for any given transposon cassette in a backbone vector the selectable marker in the transposon cassette is different from the selectable marker present in the backbone vector (e.g., kanamycin resistance coding sequences in the transposon (no endogenous promoter), a promoter operably linked to erythromycin resistance coding sequences in the backbone vector).

For example, the present invention may employ an antibiotic effective against the host organism, and the genes or set of genes that confer resistance against that antibiotic, as a selectable marker. In particular, an antibiotic resistance coding sequence is typically inserted immediately adjacent to the luxABCDE cassette within the IR regions of the transposon, in order to facilitate selection of host cells that have undergone transposition events. In this respect, kanamycin and the kanamycin resistance gene are particularly preferred. However, a variety of other antibiotic resistance genes may also be advantageously employed. They include, but are not limited to genes encoding products which confer resistance to the following antibiotics: actinomycin; ampicillan, chloramphenicol; erythromycin; gentamicin sulfate; hygromycin; neomycin; penicillin;; polymixin B sulfate; and streptomycin sulfate. Alternatively, other selection systems may be used, including but not limited to, metabolic selection, repressor proteins, and others.

In the practice of the present invention, there will typically be no promoter endogenous to the transposon that mediates transcription of the selectable marker coding sequence. However, other regulatory sequences necessary for transcription and translation to occur (e.g., an initiation codon, an open reading frame, a translation enhancing sequence, a ribosome binding site, etc.) will be present. Further, the selectable marker employed as part of the transposon will typically be inserted in the same orientation as the luxABCDE cassette, i.e., in the orientation opposite that of the transposase gene (such that transcription of the transposase gene does not result in transcription of the selectable marker/lux genes). Still further, the selectable marker sequence will typically be inserted downstream of the luxABCDE cassette, either immediately adjacent or in close proximity to that cassette, such that the sequences are operably linked in that transcription of the two is coupled, preferably tightly coupled. Hence, the encoded marker protein will not be expressed unless and until integration of the transposable sequence behind an active promoter region in the host organism's genome (i.e., operably linked to an endogenous promoter).

4. Vector Backbones

The transposon cassettes are typically cloned into shuttle vectors for ease of manipulation and isolation of large quantities of vector DNA. A number of such shuttle vectors are commonly available, e.g., pAUL-A (Chakraborty, et al. (1992) *J. Bacteriol.* 174:568–574) (a schematic diagram of the vector is presented in FIG. 1); pE194 (Sozhamannan, s., et al. (1990) *J. Bacteriol.* 172: 4543–4548; see the ATCC website on the Internet for a map of this vector; see the ATCC website on the Internet for the full sequence); pMK4 (Sullivan, M., et al, (1984) *Gene* 29:21–26), pDL289 (Buckley, N., et al., (1995) *J. Bacteriol* 177:5028–5034), pSK+ BLUESCRIPT (Clontech, Palo Alto, Calif.; Stratagene, La Jolla, Calif.); and the pSUM series mycobacteria shuttle vector (Ainsa, J. A., et al., (1996) *Gene* 176:23–26). In preferred embodiments, the shuttle vectors preferably include the following features: (1) a Gram-positive origin of replication, and/or a Gram-negative origin of replication, and/or an origin or replication functional in both types of organisms; (2) polylinkers; and (3) a polynucleotide encoding a selectable marker (e.g., ampicillin, chloramphenicol, erythromycin, and others as discussed supra) which allows selection in the host cells. Most preferably, the shuttle vectors will further include (4) transcription termination sequences flanking one or both sides of the transposon cassette. Such transcription termination sequences are used to prevent transcriptional read-through into the coding sequences of the transposon cassette.

In the preferred embodiment where the origin of replication is functional in both Gram-negative and Gram-positive organisms, the presence of a Gram-negative origin of replication permits replication of the vector in Gram-negative organisms, thereby facilitating manipulation of the inserted sequences while avoiding the restriction endonuclease systems of Gram-positive host organisms, as well as permitting isolation of large quantities of vector construct DNA. Manipulation is further facilitated by the presence of the selectable marker coding sequence operably linked to a transcriptional promoter, which permits selection of cells carrying the vector construct. As noted above selectable marker coding sequences in the transposon cassette are not typically operably linked to a promoter in vector/cassette constructs.

Alternatively, an origin of replication may be employed that is functional in both Gram-positive and Gram-negative organisms, e.g., the origins of replication present in certain Streptomyces plasmids (such as, pCK1).

The Gram-positive origin of replication may be either continuously active or may instead be conditional, e.g., the temperature-sensitive origin from pE194, as is found in the pAUL-A shuttle vector. An advantage of including a conditional origin of replication in the vector constructs of the present invention is that such elements permit stabilization of the vector construct in the host organism of interest grown under permissive conditions, while permitting the host organism to be "cured" of the vector when grown under restrictive conditions (e.g., temperature elevated to a non-permissive level).

In another aspect of the present invention, instead of using conventional selection or screening methods to determine the presence of a vector in a transformed cell, a light-based screening method may also be employed. In this embodiment, a light generating polypeptide coding sequence is placed under the control of a promoter active in an organism of interest. Such control elements may be constitutive or conditional. For example, the luxABCDE cassette, operably linked to a promoter sequence functional in the target organism of interest may be introduced into a suitable vector. The organism of interest is then transformed and the resulting organisms are screened for their ability to produce light. In this method, the production of light is used to identify transformants of interest. Light producing colonies (or patches of bacteria) are typically cloned (i.e., physically isolated) by standard methods (e.g., dilution plating, for example, using microtiter wells, or streaking for single colonies). One aspect of the present invention provides a vector comprising light-generating polypeptide sequences operably linked to promoter sequences functional in a target organism of interest. Using such a vector provides means for the transformation of organisms for which no selectable marker (such as a drug resistance marker) is available.

In one aspect of the present invention, vector backbones possess transcription termination sequences flanking one or both sides of the transposon cassette, for the purpose of preventing expression of the light generating polypeptide prior to integration of the cassette into the host organism's DNA. Such regions are known in the art. See e.g., Henkin, T. M., (1996) *Ann Rev Genet* 30:35–37; MacDonald L. E., et al. (1993) *J. Mol. Biol.* 232:1030–1037; Jeng, S. T., et al. (1997) *Can J Microbiol* 43:1147–1156.

In a preferred embodiment of the present invention, the luciferase expression cassettes are inserted into the pAUL-A shuttle vector. This vector backbone contains, inter alia, (1) a Gram negative origin of replication, (2) a conditional (temperature-sensitive) Gram-positive origin of replication, and (3) an erythromycin-resistance coding sequence, in addition to (4) a lacZ coding sequence containing (5) a polylinker region and (6) transcription termination regions. See FIG. 3.

5. Methods of Making Luciferase Transposon Cassettes and Shuttle Vector Constructs The gene cassettes, transposon cassettes and shuttle vector constructs described herein can be assembled utilizing methodologies known in the art of molecular biology (see, for example, Ausubel, F. M., et al., *Current Protocols in Molecular Biology,* John Wiley and Sons, Inc., Media, Pa. (1995), or Sambrook, et al.) in view of the teachings of the present specification.

Typically, gene cassettes comprising sequences encoding light-generating polypeptides (e.g., lux genes) are assembled. In one embodiment the sequences are assembled from polynuclotides encoding lux or luc genes by operably linking these polynucleotides to translational regulatory elements (e.g., Gram-positive Shine-Dalgarno sequences). Short, random nucleotide sequences, selectable markers, and the like can also be introduced into the expression cassettes at suitable positions.

A preferred method of obtaining polynucleotides, suitable regulatory sequences and short, random nucleotide sequences is PCR. General procedures for PCR as taught in MacPherson et al., PCR: *A PRACTICAL APPROACH,* (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. Exemplary primers are described below in Example 1. After amplification, the resulting fragments can be detected by agarose gel electrophoresis followed by visualization with ethidium bromide staining and ultraviolet illumination.

Another method for obtaining polynucleotides, for example, short, random nucleotide sequences, is by enzymatic digestion. As described below in the Examples, short DNA sequences generated by digestion of DNA from a suitable bacterium with, e.g., a blunt-cutting four-nucleotide recognition restriction enzyme such as AluI, HaeIII and Sau3AI, were ligated with the modified lux cassette. In this way translational enhancing sequences, for example, may be obtained.

Lux gene cassettes are inserted into transposon sequences typically between the first and second inverted repeats, and transposon constructs are inserted into vector backbones, using methods known in the art. For example, insert and vector DNA can be contacted, under suitable conditions, with a restriction enzyme to create complementary or blunt ends on each molecule that can pair with each other and be joined with a ligase. Alternatively, synthetic nucleic acid linkers can be ligated to the termini of a polynucleotide. These synthetic linkers can contain nucleic acid sequences that correspond to a particular restriction site in the vector DNA. Other means are known and available in the art as well.

In one aspect of the invention, the transposase coding sequences are located between the first and second inverted repeats of the transposon. In other embodiments, however, the transposase coding sequences and associated promoter may be moved from within the confines of the transposable sequences (typically defined as sequences framed by the first and second inverted repeat sequences) and placed instead on the vector backbone.

6. Evaluation of Light-Generating Polypeptide Sequences in Bacterial Cell Culture The luciferase vector constructs such as the ones described above and in the Examples, can be used to transform a variety of procaryotic host cells, including Gram-negative bacteria, Gram-positive bacteria. and other genera not included in either of the preceding classifications (e.g., *Rickettsia* spp.; *Rochalimaea* spp,; *Coxiella* spp.; *Treponema* spp., including *Treponema pallidum,* the organism which causes syphilis; *Mycoplasma* spp., and *Chlamydia* spp.).

With respect to Gram-negative host cells, the constructs of the present invention may be used to transform organisms including but not limited to the following: *Clostridium* spp., *Vibrio* spp., *Brucelle* spp., *Bordetella* spp., *Campylobacter* spp., *Pseudomonas* spp., *Escherichia* spp., *Enterobacter* spp., *Klebsiella* spp., *Serratia* spp., *Citrobacter* spp., *Proteus* spp., *Salmonella* spp., *Shigella* spp., and *Yersinia* spp.

With respect to Gram-positive host cells, the constructs of the present invention may be used to transform organisms including but not limited to the following:

Members of the Gram-positive cocci families *Micrococcaceae* (*Micrococcus* spp., *Stomatococcus* spp., *Planococcus* spp., and *Staphylococcus* spp.), *Deinococcaceae* (*Deinococcus* spp.), and species of other cocci genera including: *Streptococcus* spp (e.g., pyogenic hemolytic *streptococci* spp., oral *streptococci* spp., *Enterococci* spp., lactic acid *streptococci* spp., anaerobic *Streptococci* spp., and other species of *Streptococci*); *Leuconostoc* spp., *Pediococcus* spp., *Aerococcus* spp., *Gemella* spp., *Peptococcus* spp., *Peptostreptococcus* spp., *Ruminococcus* spp., *Coprococcus* spp., and species of the genus *Sarcina.*

Endospore-forming Gram-positive rods and cocci including: *Bacillus* spp., *Sporolactobacillus* spp., *Clostridium* spp., *Desulfotomaculum* spp., *Sporosarcina* spp., and species of the genus *Oscillospira.*

Regular, nonsporing, Gram-positive rods, including *Lactobacillus* spp., *Listeria* spp. (including the pathogenic species *Listeria monocytogenes* found as contaminants in foodstuffs, in drinking water, and on food preparation surfaces), Genus *Erysipelothrix* spp., *Brochothrix* spp., *Renibacterium* spp., *Kurthia* spp., and species of the genus *Caryophanon.*

Irregular, nonsporing, Gram-positive rods, including *Corynebacterium* (including the plant pathogenic species of *Corynebacterium, Gardnerella* spp., *Arcanabacterium* spp., *Arthrobacter* spp., *Brevibacterium* spp., *Curtabacterium* spp., *Caseabacter* spp., *Microbacterium* spp., *Aureabacterium* spp., *Cellulomonas* spp., *Agromyces* spp., *Arachnia* spp., *Rothia* spp., *Propionibacterium* spp., *Eubacterium* spp., *Acetobacterium* spp., *Lachnospira* spp., *Butyrivibrio* spp., *Thermoanaerobacter* spp., *Actinomyces* spp., and species of the genus *Bifidobacterium.*

Organisms of the family Mycobacteriaceae, i.e., *Mycobacterium* spp.

The nocardioforms, including *Nocardia* spp., *Rhodococcus* spp., *Nocardioides* spp., *Pseudonocardia* spp., *Oerskovia* spp., *Saccharopolyspora* spp., *Micropolyspora* spp., *Promicromonospora* spp., and species of the genus *Intrasporangium.*

Organisms of especial interest include: *Clostridium* spp., *Vibrio* spp., *Brucelle* spp., *Bordetella* spp., *Campylobacter* spp., *Pseudomonas* spp., *Escherichia* spp., *Enterobacter* spp., *Klebsiella* spp., *Serratia* spp., *Citrobacter* spp., *Proteus* spp., *Salmonella* spp., *Shigella* spp., and *Yersinia* spp.

Transformation methods for both prokaryotic cells and eukaryotic cells are known in the art (e.g., Sambrook, et al.) and include, but are not limited to, calcium phosphate precipitation, microinjection or electroporation. Vectors containing the appropriate regulatory elements and multiple cloning sites are widely commercially available (e.g., Stratagene, La Jolla, Calif.; Clontech, Palo Alto, Calif.) and can be used as backbone vectors to carry the transposon cassette sequences.

As described above, certain expression cassettes described herein require the addition of exogenous substrate for the production of light (e.g., luc and luxAB expression cassettes). In one embodiment of the present invention, the luciferin substrate is aldehyde. Based on the luciferase being used the appropriate luciferin substrate is selected. When administered to cells, aldehyde may be applied in the atmosphere surrounding the culture media as a vapor or directly to the culture media as a liquid or solid.

Detection and quantification of bioluminescence is accomplished using either an intensified photon-counting camera (Hamamatsu Photonics Model 2400-32) or a cooled integrating camera (Princeton Instruments Model LN/CCD 1340-1300-EB/1), as described infra.

Multiple transposon cassettes of the present invention may be incorporated into a single organism using the constructs and methods described herein. In one embodiment, each transposon cassette may encode a light generating polypeptide which emits light at a different characteristic wavelength relative to each other. Alternatively, several transposon cassettes carrying light generating polypeptides which emit light at the characteristic wavelength may be used. Combinations of transposon cassettes having a variety of such mixtures of light generating polypeptides which emit light at a different characteristic wavelengths may be constructed in view of the teachings of the present specification.

7. EVALUATION OF LUCIFERASE EXPRESSION VECTORS IN ANIMALS

Microorganisms carrying the transposon constructs described herein are particularly useful for non-invasive imaging in whole animals. Non-invasive imaging in whole animals is described in co-owned U.S. Pat. No. 5,650,135, by Contag, et al., and herein incorporated by reference. (see, also, Contag, et al., (1998) *Nature Medicine* 4(2):245–247; Contag, et al, (1996) *OSA Tops on Biomedical Optical Spectroscopy and Diagnostics* 3:220–224; Contag, et al., (1997) *Photochemistry and Photobiology*, 66(4):523–531; and Contag, et al., (1995) *Mol. Microbiol.* 18:593–603.

In the imaging method, the conjugates contain a biocompatible entity (e.g., a transformed bacterium carrying a transposon of the present invention integrated into its genome) and a light-generating moiety (e.g., a luciferase enzyme). Light-emitting conjugates are typically administered to a subject by any of a variety of methods, allowed to localize within the subject, and imaged. Since the imaging, or measuring photon emission from the subject, may last up to tens of minutes, the subject is typically, but not necessarily, immobilized during the imaging process.

Imaging of the light-emitting entities involves the use of a photo detector capable of detecting extremely low levels of light—typically single photon events—and integrating photon emission until an image can be constructed. Examples of such sensitive photo detectors include devices that intensify the single photon events before the events are detected by a camera, and cameras (cooled, for example, with liquid nitrogen) that are capable of detecting single photons over the background noise inherent in a detection system.

Once a photon emission image is generated, it is typically expressed as a pseudocolor image superimposed on a "photographic" reflected light image of the subject to provide a frame of reference for the source of the emitted photons (i.e. localize the light-emitting conjugates with respect to the subject). Such a "composite" image is then analyzed to determine the location and/or level of expression of a reporter gene in the subject.

7A. Infection of Animals

The Tn4001 lux km$^R$ cassettes described herein are useful in evaluating various procaryotic cells in an animal. For example, the cassettes described can be integrated into the genome of pathogenic bacteria (e.g., Gram-positive bacteria) previously described and subsequently introduced into a whole animal. The animal can then be used to follow the infection process in vivo and to evaluate potential anti-infective drugs, such as new antibiotics, for their efficacy in inhibiting the infection. Thus, in one aspect, the expression cassettes described herein are useful in non-invasive imaging and/or detecting of light-emitting conjugates in mammalian subjects infected with bacteria carrying a luciferase expression cassette. By way of example, the lux transposon cassettes can be used to screen agents useful in inhibiting the growth and/or proliferation of pathogenic bacteria.

In addition, it is possible to obtain *E. coli* libraries containing bacteria expressing surface-bound antibodies which can be screened to identify a colony expressing an antibody against a selected antigen (Stratagene, La Jolla, Calif.). Bacteria from this colony can then be transformed with a lux transposon cassette of the present invention, and transformants having undergone at least one transposition event can be utilized in the methods of the present invention, as described above, to localize the antigen in a mammalian host.

Alternatively, the transformed cells may be administered to a test subject such that they become uniformly distributed in the subject.

7B. Sustrate Administration

As described above, certain expression cassettes described herein require the addition of exogenous substrate for the production of light (e.g., luc and luxAB expression cassettes). In a preferred embodiment of the present invention, the substrate is aldehyde. The substrate may also be administered to the whole animals. Appropriate concentrations for the substrate can be empirically determined for each line of test animal constructed. The substrate (typically, luciferin or aldehyde) can be administered before, concomitantly with, or after the administration of the analyte of interest. The routes of administration of the substrate can be as described for the analyte. Preferred routes of administration for the substrate include, but are not limited to, intravenous or topical administration or by providing substrate in the atmosphere, for example, as a vapor.

8. Uses of the Constructs of the Present Invention

The following is a general description of how and why the present invention works. Although applicants do not intend to be bound by the mechanism described, it is included in order to allow a more clear understanding of the present invention, and of the uses to which it may be put.

As discussed supra, the sequences of interest present in the transposon cassettes of the present invention lack the associated promoter sequences necessary to allow their transcription in the target organism. Manifestation of the phenotypic characteristics encoded by the sequences of interest in organisms transformed with the Tn4001 lux km$^R$ shuttle vector constructs are therefore likely due to incorporation of the transposable unit within the genome of the target organism. In particular, the sequences of interest have likely integrated in such as way as to have become operably linked to an active promoter present in the host organism's genome (i.e., a promoter endogenous to the host organism).

The transposon cassette of the present invention is useful in a wide variety of applications. For example, they may be employed in methods of modifying a target organism.

In a preferred embodiment of the present invention, pAUL-A Tn4001 luxABCDE km$^R$ shuttle vector constructs are used to modify an organism of interest. Bacterial cells of interest are transformed with the shuttle vector construct via, for example, electroporation, or phage-mediated transduction or conjugation. Transformed cells carrying the shuttle vector may be selected and maintained by means of growing the electroporated cells on media containing erythromycin. Cells wherein the luxABCDE km$^R$ coding cassette has integrated behind active promoter regions in the host organism's genome may be selected and maintained by means of culturing erythromycin-resistant transformants on media containing kanamycin: integrant cells will give rise to bioluminescent, kanamycin-resistant colonies. See Examples 6 and 7.

Organisms modified with the pAUL-A Tn4001 luxAB-CDEY km$^R$ shuttle vector construct may be modified as above with the exception that the bioluminescence exhibited by those cells is of a different wavelength.

In another embodiment, a pAUL-A shuttle vector comprising the luxAB transposon cassette is employed as above, with the exception that organisms capable of exhibiting the bioluminescent phenotype will be detected by first exposing them to exogenous aldehyde substrate, as described above.

Constitutively bioluminescent organisms may be prepared and identified by this method. See Examples 5 and 6, infra. Alternatively, conditionally bioluminescent organisms may also be identified as above, with the exception that selection of the conditionally bioluminescent transposants is accomplished by first replica-plating erythromycin-resistant transformants on culture media containing kanamycin, then growing the plates of a replica pair under restrictive and permissive conditions, respectively, and finally identifying colonies which exhibit a bioluminescent, kanamycin-resistant phenotype only when grown under permissive conditions. See Example 7. One example of conditional promoters identified by this method are heat-shock promoters, where the restrictive temperature is typically 42° C. and the permissive temperature can be, for example, room temperature to 37° C. Conditional promoters may also be associated with growth phase, stage of infection, and quorum sensing, pathogenicity, stage of life cycle (cyst formation or reproduction), growth conditions, etc.

Genes specifically involved in the pathogenesis of various organisms of interest (e.g., pathogenic Gram-positive organisms, *Chlamydia, Treponema pallidum,* etc.) may be identified using the shuttle vector constructs of the present invention in conjunction with in vivo expression technology. In a preferred embodiment, a strain of pathogenic bacteria, transformed with the Tn4001 lux km$^R$ shuttle vector construct and grown under conditions for maintaining the construct, is injected into an experimental animal, such as a mouse. Transposants which have integrated the lux km$^R$ cassette next to promoters active in, for example, the early stages of pathogenesis are then selected for by injecting the animal with kanamycin shortly after infection, plating on non-selective media, and selecting dark colonies. This step insures that the transposition of the transposon cassette into the genome has not resulted in the association of the transposon with a constitutive promoter. After culturing the colonies and injecting them into experimental animals, bacterial promoters active in pathogenesis are identified by monitoring the animals for light production. See Example 9.

Owing to the close-coupling of the lux km$^R$ cassette with active promoter regions in the bioluminescent transposants of interest, it is possible to identify and sequence both the promoter region and the gene coding sequence normally associated with those promoters in the host cell genome by methods known to persons of ordinary skill in the art in view of the teachings of the present specification. PCR amplification and subsequent sequencing of the amplification products may be employed, using primers based on gene sequences present in the integrated luxABCDE km$^R$ cassette. Alternately, the promoter may also be sequenced by directly isolating chromosomal DNA from a single bioluminescent bacterial colony of interest, and then sequencing using primers specific for regions of the kanamycin resistance gene adjacent or in close proximity to the promoter sequence of interest. The associated gene sequences may also be isolated and sequenced by these methods. See Example 10.

Integrants wherein the lux km$^R$ cassette is operably linked to promoters active during pathogenesis may be used to identify effective pharmaceutical agents and determine their point of action. After isolating a panel of transposants corresponding to the family of promoters activated during pathogenesis (for example, different stages of infection or different stages of the infectious organisms' life cycle) by the methods described in Example 9, that panel is used to infect multiple groups of experimental animals, each group corresponding to a particular promoter/gene of interest. The group is then treated with the pharmaceutical agent of interest, and both the experimental animals and infected, untreated control animals are then monitored for bioluminescence. Agents effective in suppressing transcription and/or translation (either directly or indirectly) or that perturb the ability of the transposant to function normally (such as disruption of the cell wall) will suppress bioluminescence in the treated experimental animals, while bioluminescence will be observed in the corresponding infected, untreated control animals. See Example 11.

The relative strength of promoter activity may be determined, either by means of replica plating onto culture media containing increasing concentrations of antibiotic, or by employing "crippled" antibiotic genes as the selective marker in the transposon cassette. For example, a modified neomycin resistance gene can be employed where in order to get resistance to the antibiotic a high-level of expression of the neomycin resistance gene is required. In one embodiment the crippled selectable marker is a neomycin resistance (Neo$^r$) sequence in which amino acid residue 182 (Glu) is mutated to Asp. (Yanofsky, et al., (1990) PNAS USA 87:3435–39). Use of such crippled selectable markers improves the strength of the selection, because more of the enzyme is required to produce antibiotic resistance. See Example 12.

The constructs of the present invention are useful in methods designed to monitor bacterial growth in foodstuffs. The contamination of foodstuffs, cosmetics, pharmaceuticals and the like by undesirable micro-organisms represents a significant threat to public health.

In the past a number of methods to monitor the presence of such micro-organisms in, for example, foodstuffs, water supplies and on food preparation surfaces have been developed. These methods generally rely on conventional microbiological techniques, including the growth of micro-organisms on selective nutrient solid support media or alternatively in selective nutrient media. Morphological analyses are usually carried out. Testing methods such as these are hindered by the fact that results may not be obtained for 24 to 48 hours or more. Further, the process is complex and laborious.

Alternative techniques have been developed based on the growth of microorganisms in nutrient media in the presence of an indicator specific to a selected microorganism that is to be detected. Approximately 12 to 24 hours is still required for a result to be obtained in such testing assays. During all aspects of the preparation of food for human consumption such time limitations are undesirable.

Organisms modified to produce light as taught by the present invention can be used to monitor the presence of microorganisms, for example, in foodstuffs, in drinking water, and on food preparation surfaces. Potential applications in this context include, but are not limited to, the following:

1) Monitoring growth of Gram-positive pathogens and spoilage bacterium in foods and beverages;
2) Monitoring and tracking Gram-positive pathogens and spoilage bacterium in food production plants and dairies, and the spread of such pathogens amongst animals on farms and in the environment, i.e., contamination route analysis;
3) Development of food preservation techniques and compounds that are specific to different Gram-positive pathogens and spoilage bacterium;
4) Testing material subjected to the above said food preservation techniques and compounds in animals to ensure such treatments do not increase the pathogenicity of the bacterium being tested;
5) Incorporation of luxAB and luxABCDE into bacteriophage to enable the identification and quantification of specific Gram-positive pathogens and spoilage bacterium in foods and beverages. For example, the method outlined in Scherer et al., U.S. Pat. No. 5,824,468 in combination with the constructs of the present invention may be employed in view of the teachings of the present specification;
6) Monitoring genetic transfer of DNA amongst Gram-positive pathogens in foods fed to animals, with and without antibiotic pressure/selection;
7) Monitoring of antibiotics in foods, especially meat and dairy products; and
8) Development of biodetectors by tagging genes in Gram-positive bacteria that respond to environmental stresses or biological/chemical compounds.

For example, a light-generating organism of the present invention can be used to, for example, seed a food product. Then the food product can be treating using a particular sterilization method (e.g., X-rays, heat processing, pasturizing, microwaves, etc.). The efficacy of the sterilization method can then be evaluated by examining light production (or the absence thereof) from microorganisms in the food product. The light-generating organisms of the present invention may be used to evaluate the proliferation of such organisms in any selected medium, as well as, whether treatments (e.g., the addition of compounds such as antimicrobials) are efficacious at stopping the proliferation of such organisms in the selected medium.

The wide variety of modified microorganisms produced using the constructs and methods of the present invention may be used in conjunction with the in vivo expression technology methods described below. See Example 13.

Below are examples of specific embodiments for carrying out the present invention. The examples are offered for illustrative purposes only, and are not intended to limit the scope of the present invention in any way.

Materials and Methods

Unless indicated otherwise, manipulation of cells, proteins and nucleic acids (e.g., DNA) were performed using standard methods, as described in, e.g., Sambrook, et al., and Ausubel, F. M., et al., *Current Protocols in Molecular Biology*, John Wiley and Sons, Inc., Media, Pa. (1995). Unless indicated otherwise, restriction enzymes were obtained from New England Biolabs, modifying enzymes were obtained from Promega or Boehringer Mannheim, and other laboratory chemicals were obtained from Sigma Chemical Company (St. Louis, Mo.).

Efforts have been made to ensure accuracy with respect to numbers used (e.g., amounts, temperatures, etc.), but some experimental error and deviation should, of course, be allowed for.

A. In Vitro Screening in Presence of Exogenous Aldehyde

Exogenous aldehyde substrate was added prior to imaging plates or cultures of bacteria not containing the luxCDE genes. For imaging plates, n-decyl aldehyde (decanal; Sigma Chemical Company) was spread on the inside surface of lids covering the plates containing the bacteria to be imaged ("aldehyde vapor imaging"), and the plates then imaged using an intensified CCD camera (Hamamatsu Photonics model 2400-32) essentially as described in U.S. Pat. No. 5,650,135. For imaging liquid cultures, 1 µl of a 1% decanal solution (in 50% ethanol) was added to 1 ml of the appropriate 10-fold dilutions of the culture.

B. Preparation of DNA and Cloning

Unless indicated otherwise, following digestion with one or more restriction endonucleases, DNA samples were heated to 85° C. for 15 min to inactivate the restriction enzymes. Ligations were performed at 16° C. overnight.

C. Transformation of Bacterial Cells

Preparation of Competent Cells. Unless indicated otherwise, bacterial cells were transformed as follows. Bacterial cultures were grown overnight in LB. Five ml of each culture were used to inoculate fresh 500 ml volumes of LB. These cultures were shaken at 37° C. until an O.D (600 nm) of approximately 0.6 was reached. The cells were then chilled on ice for 30 min before being harvested by centrifugation at 3,000×g for 10 min at 4° C. The cells were resuspended in 50 ml of either cold 0.5 M sucrose (*S. aureus*) or ddH$_2$O (*E. coli*), before being re-centrifuged and resuspended in 5 ml of either cold 0.5 M sucrose (*S. aureus*) or ddH$_2$O (*E. coli*). At this stage, the cells were held on ice for 30 min, and then re-centrifuged and resuspended in 5 ml of cold 10% glycerol. Aliquots of each cell type were frozen down and stored at −80° C.

Electroporation. Plasmid DNA was purified using a Qiagen column, dialyzed, and electroporated into competent cells using a "GenePulser" (BioRad). The settings were 25 µF, 2.5 kV, and either 100 ohms resistance for *S. aureus*, or 400 ohm resistance for *E. coli* and *S. pneumoniae*. The cells were left to recover in 1 ml of culture medium 2 hr at 37° C. before being plated on a suitable agar containing the requisite selection antibiotic.

D. Imaging Samples

Samples were imaged essentially as described in Contag, et al., U.S. Pat. No. 5,650,135, with minor modifications as indicated below.

In experiments performed in support of the present invention (detailed below), the amount of light generated by a sample was quantified using either an intensified photon-counting camera (Hamamatsu Photonics Model 2400-32) or a cooled integrating camera. With respect to the cooled integrating type of camera, the particular instrument used was selected from among three makes/models: (1) Princeton Instruments Model LN/CCD 1340-1300-EB/1; (2) Roper model LN-1300EB cooled CCD camera (available from Roper Scientific, Inc., Tucson, Ariz.); and (3) Spectral Instruments model 600 cooled CCD camera (available from Spectral Instruments, Inc., Tucson, Ariz.). The preferred apparatus was the Hamamatsu Photonics camera number XEN-3 and the Princeton Instruments camera number XEN-5, respectively, both located at Xenogen Corporation, Alameda, Calif. Both types of cameras use a charge-coupled device array (CCD array), to generate a signal proportional to the number of photons per selected unit area. The selected unit area may be as small as that detected by a single CCD pixel, or, if binning is used, that detected by any selected group of pixels. This signal may optionally be routed through an image processor, such as the Argus available from Hamamatsu Photonics, and is then transmitted to a computer (either a PC running Windows NT (Dell Computer Corporation; Microsoft Corporation, Redmond, Wash.) or a Macintosh (Apple Computer, Cupertino, Calif.) running an image-processing software application, such as "LivingImage" (Xenogen Corporation, Alameda, Calif.). The software and/or image processor are used to acquire an image, stored as a computer data file. The data generally take the form of (x, y, z) values, where x and y represent the spatial coordinates of the point or area from which the signal was collected, and z represents the amount of signal at that point or area, expressed as "Relative Light Units (RLUs).

To facilitate interpretation, the data are typically displayed as a "pseudocolor" image, where a color spectrum is used to denote the z value (amount of signal) at a particular point. Further, the pseudocolor signal image is typically superimposed over a reflected light or "photographic" image to provide a frame of reference.

It will be appreciated that if the signal is acquired on a camera that has been calibrated using a stable photo-emission standard (available from, e.g., Xenogen Corporation), the RLU signal values from any camera can be compared to the RLUs from any other camera that has been calibrated using the same photo-emission standard. Further, after calibrating the photo-emission standard for an absolute photon flux (photons emitted from a unit area in a unit of time), one of skill in the art can convert the RLU values from any such camera to photon flux values, which then allows for the estimation of the number of photons emitted by a transformed cell in the sample per unit time.

E. Quantification of Light Output Using 96-Well Microtiter Plates

The amount of light generated by cells in solution was quantified by plating dilutions of the solution into wells of a 96-well plate, and imaging the plate as described above in the Xen-3 camera. The LivingImage software was then used to superimpose defined borders around the each area of the image showing a signal corresponding to light from a particular well. The signal from each of these areas was then quantified, and expressed as a single RLU value for each well. These RLUs were used in several of the studies detailed below, including Examples 13, 14 and 15.

EXAMPLE 1

Incorporation of Gram-positive RBS Upstream of luxA, B, C, D and E

The five genes of the *Photorhabdus luminescens* lux operon, lux A–E, were PCR amplified using the polymerase chain reaction (PCR; Mullis, et al., U.S. Pat. No. 4,683,195; Mullis, U.S. Pat. No. 4,683,202) to incorporate the sequence of the Gram-positive ribosome binding site (RBS) AGGAGG (SEQ ID NO:1) such that this site was at least seven nucleotides upstream of each start codon. Each of the lux genes was amplified individually using the primer sets shown in Table 1, below. In each case, nucleotides highlighted in bold show the position and sequence of the different restriction endonuclease sites (identified in far-right column) incorporated to facilitate cloning. Gram-positive RBSs, and start/stop codons (ATG/TAA) are underscored by solid and broken lines, respectively.

TABLE 1

| Gene | Primer | SEQ ID No: | Sequence | Restriction Sites |
|---|---|---|---|---|
| luxA | XAF | 2 | CCCCGGATCCTGCAGATGAAGCAAGAGGAGGACTCTCTATG | BamH I, PstI I |
|  | XAR | 3 | GGCGGATCCGTCGACTTAATATAATAGCGAACGTTG | BamH I, Sal I |
| luxB | XBF | 4 | GGGAATTCTCGAGGAGGAGAGAAAGAAATGAAATTTGGA | EcoR I, Xho I |
|  | XBR | 5 | GGCGGATCCGTCGACTTAGGTATATTCCATGTGGTAC | BamH I, Sal I |
| luxC | XCF | 6 | GGGAATTCTCGAGGAGGATGGCAAATATGACTAA | EcoR I, Xho I |
|  | XCR | 7 | GGCGGATCCGTCGACTTATGGGACAAATACAAGGAAC | BamH I, Sal I |
| luxD | XDF | 8 | GGGAATTCTCGAGGAGGAGTAAAAGTATGGAAAATGA | EcoR I, Xho I |
|  | XDR | 9 | GGCGGATCCGTCGACTTAAGACAGAGAAATTGCTTGA | BamH I, Sal I |
| luxE | XEF | 10 | GGGAATTCTCGAGGAGGAAAACAGGTATGACTTCATAG | EcoR I, Xho I |
|  | XER | 11 | GGCGGATCCGTCGACTTAACTATCAAACGCTTCGGTTA | BamH I, Sal I |

PCR was performed with an automated thermocycler (Techne Progene, Princeton, N.J.) with 200 μl thin walled PCR tubes (Molecular BioProducts, San Diego, Calif.). Reactions were carried out in 50 μl volumes containing 5 μl of 10X PCR buffer (supplied with Taq DNA polymerase obtained from Roche Molecular Biochemicals (Switzerland), 2.0 mM MgCl$_2$, 50 pmol of each oligonucleotide primer (Operon; see Table 1 for sequences), 0.2 mM of each deoxynucleotide triphosphate (dATP, dCTP, dGTP, dTTP; Amersham Pharmacia Biotech, (Uppsala, Sweden)), 1 U of Taq DNA polymerase Roche Molecular Biochemicals (Switzerland), and 10 ng of plasmid DNA containing the *P. luminescens* luxCDABE cassette (either pSB417 or pSB384; Winson, et al., (1998), *FEMS*, 163:185–202). Amplification of each gene was achieved using 30 cycles at 95° C. for 15 sec., 50° C. for 30 sec., and 72° C. for 1 min., followed by a final extension step at 72° C. for 2 min.

The sequence of the *Photorhabdus luminescens* (formerly referred to as *Xenorhabdus luminescens*) luxCDABE cassette is available from GenBank, under accession number M90092.1 (GI:155411; XENLABCDEB) (Meighen, E. A. and Szittner, R., *J. Bacteriol.* 174:5371–5381 (1992)).

EXAMPLE 2

Construction of pSK⁻G+luxA+luxB (luxAB Cassette in pBluescript SK⁻)

The genes amplified in Example 1, above, were individually assembled on pBluescript SK⁻ vectors (Stratagene, LaJolla, Calif.). The luxA PCR product was digested with BamH I/Sal I and ligated into pBluescript SK⁻ at the BamH I/Sal I sites (directionally orientated downstream of the IPTG-inducible lacZ promoter), generating plasmid pSK⁻G+luxA. Plasmid pSK⁻G+luxA was then electroporated into DH5α *E. coli* (Stratagene), and the cells were plated on LB agar plates containing 100 µg/ml ampicillin. Selected colonies were grown up for plasmid preps, and the plasmid DNA was isolated and cut with Sal I. The resulting fragments were ligated with Sal I/Xho I-cut luxB PCR amplified DNA (Example 1) to generate pSK⁻G+luxAG+luxB.

pSK⁻G+luxAG+luxB was electroporated into DH5α *E. coli* cells, plated on LB agar containing 100 µg/ml ampicillin and the resulting transformants screened for light in the presence of exogenous aldehyde (see Materials and Methods) using a photon-counting CCD camera (see Materials and Methods). Bioluminescent colonies were purified and monitored for their light intensity. Extremely high levels of bioluminescence were recorded (camera sensitivity only reaching 2.0). Even in the absence of exogenous aldehyde, background levels of light could be detected in both solution and from plates (switching the bit range from 0–5 in 1 min in the latter case). Surprisingly, the level of light from the Gram negative *E. coli* colonies containing pSK⁻ G+luxAG+ luxB was significantly greater (in the presence of exogenous aldehyde) than the level of light from *E. coli* colonies transformed with the native *Photorhabdus luminescens* lux operon.

These results show that functional *Photorhabdus luminescens* luciferase α and β subunits can be individually expressed in Gram negative bacteria (e.g., *E. coli*) from a DNA expression cassette driven by the lacZ promoter, where the DNA expression cassette contains Gram positive Shine-Dalgarno sequences upstream of each of the luxA and lux B coding sequences.

EXAMPLE 3

Construction of pSK⁻ luxABCDE (luxABCDE Cassette in pBluescript) and Expression of the Proteins Encoded by the luxABCDE Cassette in *Staphylococcus aureus*

Assembly of a separate luxCDE cassette in pBluescript SK⁻ was achieved by the sequential cloning of luxC, luxD and luxE essentially as described in Example 2 for the generation of the luxAB cassette. The luxC-E PCR amplification products were individually digested with the compatible enzymes SalI and XhoI, and each step of the cloning procedure was confirmed by PCR of the *E. coli* transformants. The fidelity of the final luxCDE cassette was confirmed by inserting this sequence, cut with Sal I/Xho I, at the Sal I site downstream of the luxAB genes in pSK⁻G+luxAG+luxB, generating pSK⁻luxABCDE. Screening was performed as described above, except that no aldehyde treatment was performed, since the substrate was encoded by the luxCDE genes. As above, *E. coli* DH5α containing pSK⁻luxABCDE were considerably brighter than bacteria containing the native *Photorhabdus luminescens* lux operon.

To demonstrate that the above luxABCDE construct is capable of being expressed in a Gram-positive organism, the construct was inserted into the Gram-positive/negative shuttle vector pMK4 (Sullivan, M. A., et al. (1984) *Gene* 29:21–26) and tested for bioluminescence in different *S. aureus* strains using random host DNA fragments as promoters.

The luxABCDE cassette was cut from pBluescript SK⁻ using the restriction enzymes BamHI and SalI, and ligated with similarly cut pMK4 plasmid DNA (orientated so that no promoter lay upstream of this cassette; FIG. 1). This ligation was electroporated into *E. coli* DH5α and luxABCDE clones, grown overnight at 37° C. on LB containing 100 µg/ml ampicillin (the Gram-negative selectable marker found on pMK4), were selected by screening for colonies emitting low levels of bioluminescence (light barely detectable using the Hamamatsu ICCD camera).

In order to place the lux cassette under the control of a Gram-positive promoter sequence, genomic DNA from a clinical isolate of methicillin resistant *S. aureus* (MRSA) was cut with Sau3A in a partial digest and ligated into pMK4 luxABCDE plasmid DNA cut with BamHI (the BamHI enzyme was left active to reduce background from re-ligation of the empty vector DNA).

To amplify the construct, this ligation mix was then electroporated into *E. coli* DH5α and the resulting transformants were plated on LB containing 100 µg/ml ampicillin. The colonies were scraped from the plates, pooled, and their plasmid DNA extracted (Plasmid Spin Miniprep Kit, Qiagen, Valencia, Calif.). This plasmid DNA was electroporated into competent *S. aureus* RN4220 cells and the resulting transformants selected on LB containing 5 µg/ml chloramphenicol (the Gram-positive selectable marker found on pMK4).

Highly bioluminescence colonies obtained using the preceding method were then selected using the ICCD camera.

From the 2000 or so bioluminescent colonies, 73 moderately to highly bioluminescent transformants were isolated and further characterized for constitutive bioluminescence. The level of bioluminescence from the majority of these strains was comparable to that seen from Gram-negative bacteria, such as *E. coli,* carrying an expressed luxCDABE operon. Bioluminescence from pure cultures of many of the latter *S. aureus* was at a level that could be observed by the naked eye in a darkroom after less than a minute of acclimatization.

Thus the luxABCDE operon is capable of being expressed in the Gram-positive organism *S. aureus* when placed under the control of a Gram-positive promoter sequence.

EXAMPLE 4

Construction of a Gram-Positive lux Transposon: Tn4001 luxABCDE km$^R$

The luxABCDE km$^R$ cassette was constructed as follows: A Gram-positive kanamycin cassette from pDL289 (Buckley, N. D., et al. (1995) *J. Bacteriol.* 177:5028–5034) was PCR amplified using the primers KanF2 (5'-CTG TAG ACT CGA GGA GGG AAA TAA TAA ATG GC; SEQ ID NO:12; the bolded letters represent a XhoI site) and KanR2 (5'-CAG AGT GTC GAC AGT TGC GGA TGT AC; SEQ ID NO:13;

the bolded letters represent a SalI site). Amplification was carried out for 30 heating/cooling cycles of 15 seconds at 95° C., 30 seconds at 50° C., and 2 minutes at 72° C.

The resulting amplification product provided a promoterless km$^R$ antibiotic resistance gene. The amplification product was then cut with XhoI/SalI and ligated into the SalI site of the pSK-luxABCDE plasmid construct (prepared in Example 3, above) directly downstream of the luxABCDE cassette.

The pSK luxABCDE km$^R$ plasmid construct was electroporated into *E. coli* DH5α cells and the transformed bacteria were plated onto LB plates containing 25 µg/ml kanamycin. After incubation at 37° C. overnight, the resulting transformants were screened for light production (see Materials and Methods) using a photon-counting CCD camera (Hamamatsu Photonics, Shizuoka Pref., Japan; model 2400-32). Expression of both kanamycin resistance and bioluminescence in *E. coli* (Gram-negative) were mediated by the lacZ promoter found in the pBluescript II SK (+/−) vector backbone. DNA was prepared from bioluminescent colonies. The correct orientation of the kanamycin cassette (i.e., the coding sequence) relative to the luxABCDE coding sequences was confirmed by restriction digestion of the DNA with SalI and analysis of the resulting restriction patterns.

Figure 2:
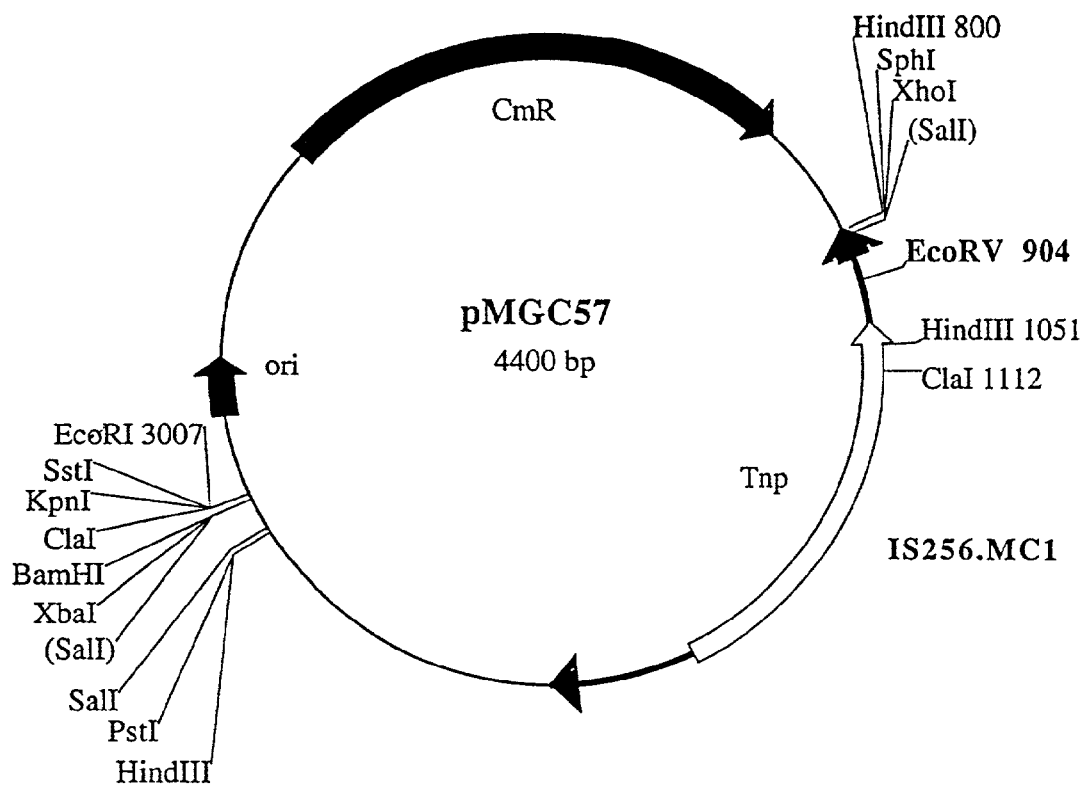
FIG. 2 presents a schematic diagram of the pMGC57 backbone vector.

To construct a Tn4001 cassette containing the lux and km$^R$ genes, the luxABCDE km$^R$ cassette was cut from the pSK luxABCDE km$^R$ construct, prepared above, using SpeI/SalI. The ends of the fragments were filled in with nucleotides to generate blunt-ended molecules. These molecules were ligated into the EcoRV site of the plasmid pMGC57 (FIG. 2; Lyon et al. (1998) *EMBO J.* 17:6263–6275) and the constructs electroporated into DH5α cells. The transformed bacteria were plated onto LB media containing 15 µg/ml chloramphenicol. The resulting transformants were screened for light production, chloramphenicol-resistance (CmR) and kanamycin-resistance (KanR). DNA was prepared from light-generating, CmR, KanR colonies. The correct orientation of the luxABCDE km$^R$ cassette, i.e., the location of the 5' end of the luxA sequence relative to the 5' end of the Tn4001 transposon, was confirmed by restriction digestion (XhoI/NdeI and XhoI/EcoRV) and restriction pattern analysis, as well as, by PCR analysis of DNA. PCR was carried out using the primers MGC-CAT-F1 (5'-GGT GTC CCT GTT GAT ACC G-3', SEQ ID NO:14) and LuxA-Rev (5'-CCA CAC TCC TCA GAG ATG CG-3', SEQ ID NO:15) under conditions detailed supra. The correct orientation was identified by fragment size.

EXAMPLE 5

Construction of Tn4001 luxABCDE km$^R$ Shuttle Vector Constructs

Experiments performed in support of the present invention indicated that it was not possible to transpose the luxABCDE km$^R$ cassette onto the chromosomes of *Staphylococcus, Listeria, Enterococcus, Bacillus*, as well as, some types of *Streptococcus* cells by simply electroporating the transposon construct of the present invention into these bacteria using the suicide vector pMGC57; a method of transposition shown to work in *Streptococcus pyogenes* (Lyon et al. (1998) *EMBO J.* 17:6263–6275). In order to overcome this limitation of the vector the following constructs were made and experiments performed.

Sequences of Tn4001 as well as its related insertion sequences (IS) are known and available as GenBank Accession Numbers X53951; X53952; M18086; and M29261 and are further described in Hahn et al. (1999) *Plasmid* 41:120–124.

A. Construction of the pAUL-A Tn4001 luxABCDE km$^R$ Shuttle Vector

The Tn4001 cassette containing the lux and km$^R$ genes (designated IR luxABCDE km$^R$ tnp IR, where, IR represents inverted repeats and tnp represents the gene encoding the Tn4001 transposase) was inserted into a broad-range shuttle vector having a gram negative origin of replication and a gram positive origin of replication (either constitutive or conditional, e.g., temperature sensitive). One example of such a shuttle vector is the pAUL-A vector (Chakraborty, et al. (1992) *J. Bacteriol.* 174:568–574) which contains an erythromycin resistance gene that is functional in both Gram-positive and Gram-negative bacteria. This vector contains both a Gram-negative origin of replication and the temperature-sensitive pE194 Gram-positive origin of replication. See FIG. 1.

Herein the transposon cassettes of the present invention are schematically represented as follows. The inverted repeats (IR) generally indicate the ends of the transposable element. Accordingly one designation for the transposon is IR- tnp-IR, where tnp designates the gene encoding the transposase. Further elements can be added to the transposon and are indicated similarly, e.g., addition of a luxABCDE km$^R$ cassette is rendered schematically as IR luxABCDE km$^R$ tnp IR.

The IR luxABCDE km$^R$ tnp IR cassette was cut from pMGC57 using the enzymes EcoRI/XhoI and ligated into the EcoRI/SalI sites of the pAUL-A shuttle vector (FIG. 3) to give the shuttle vector construct pAUL-A Tn4001 luxABCDE km$^R$.

*E. coli* cells (DHα5) were transformed with the shuttle vector construct by electroporation, plated onto LB plates containing erythromycin at a concentration of 150 µg/ml, and incubated at 37° C. overnight. The resulting transformants were screened for light production, erythromycin-resistance (EmR) and kanamycin-resistance (KanR). While expression of the lux and km$^R$ genes can in theory be mediated in *E. coli* (a Gram-negative organism) by read-through of the lacZ promoter present in the pAUL-A vector backbone owing to the presence of the transcription termination regions flanking the lacZ operon (see FIG. 3), experiments performed in support of the present invention have shown no such lacZ-mediated transcription occurs in Gram-positive host cells transformed with this vector construct. Plasmid DNA was then isolated from light-generating, ErR, KanR colonies.

Transposition of pAUL-A Tn4001 luxABCDE km$^R$ and expression of the luxABCDE cassette in a Gram-Positive organism: Next, the transposition and stability of the Tn4001 luxABCDE km$^R$ cassette in Gram-positive cells was demonstrated. The DNA prepared above was electroporated into *Staphylococcus aureus* RN4220 (see Materials and Methods). Several hundred RN4220 transformants were obtained on chocolate plates containing erythromycin at a concentration of 0.3 µg/ml. Because no promoter had been provided for transcription of the luxABCDE km$^R$ genes (in Gram-positive bacteria) of the expression cassette no light was expected to be generated by any of these colonies. No light production by any of the transformants was observed, suggesting that the luxABCDE cassette had not rearranged.

The EmR RN4220 colonies were then pooled directly from plates and plasmid DNA prepared from the pool. This DNA was then electroporated into *S. aureus* 8325-4. Numerous colonies of erythromycin resistant 8325-4 were gained. Again, no light production was observed in the EmR transformants.

Finally, the ability of the IR luxABCDE km$^R$ tnp IR cassette to transpose into the bacterial chromosomes of Gram-positive bacteria was demonstrated. Nineteen of the *S. aureus* 8325-4 erythromycin$^R$ transformants were streaked onto kanamycin plates. Two of these streaks resulted in the growth of numerous, clearly definable colonies all with varying levels of light. These colonies arose as a result of transposition of the luxA-E km$^R$ cassette onto the chromosome of 8325-4 behind active *S. aureus* 8325-4 promoters.

These results confirm that the luxABCDE km$^R$ cassette in a broad-range shuttle vector having a Gram-positive origin of replication is capable of transposing into the bacterial chromosome of a Gram-positive bacterial strain.

Figure 3:
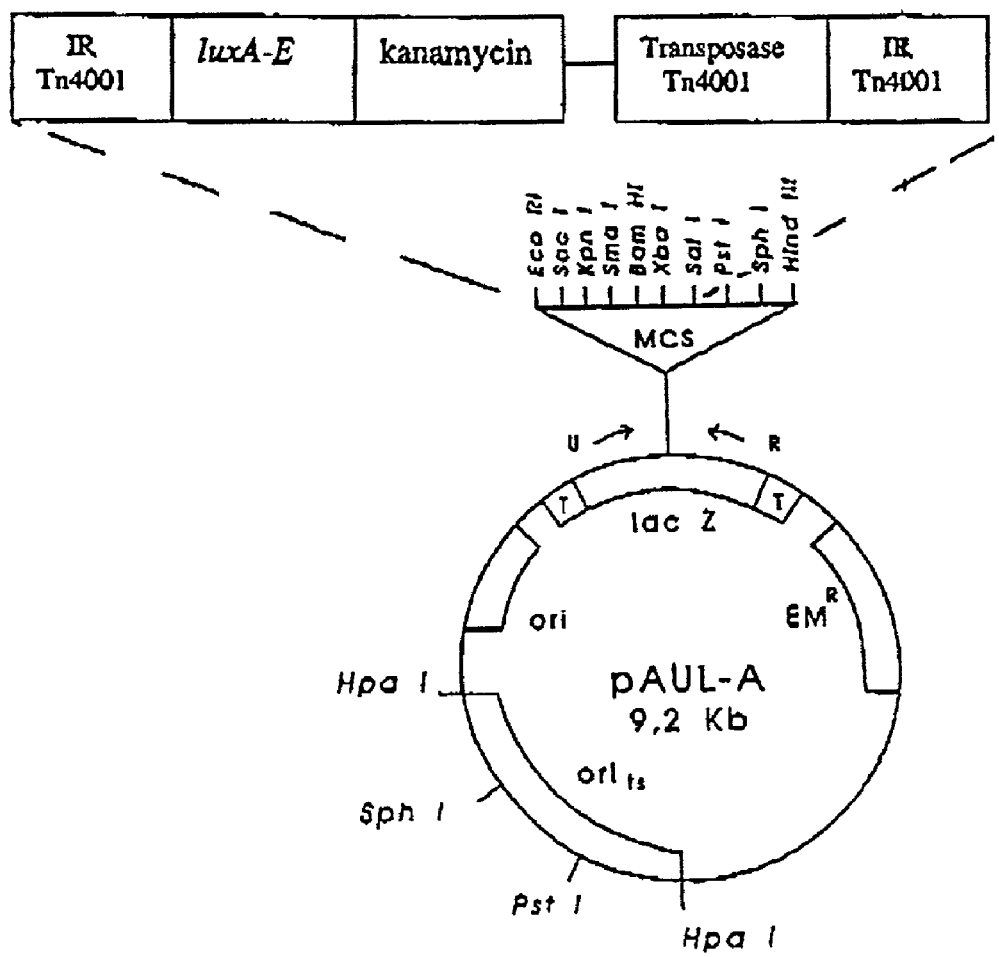
FIG. 3 presents a schematic diagram of the pAUL-A vector containing a transposon cassette of the present invention. In the figure, the vector backbone region labeled "lacZ" represents the lacZ operon; the regions labeled "T" represent transcription termination regions; "MCS" indicates the multiple cloning site present in the lacZ operon, (individual restriction endonuclease sites present therein are indicated); "ori" represents the Gram-negative origin of replication; "$ori_{ts}$" represents a temperature-sensitive pE194 Gram-positive origin of replication (restriction endonuclease recognition sites present therein are indicated); and "$EM^R$" represents the erythromycin resistance gene. In the transposon cassette, the regions labeled "IR Tn4001" represent inverted repeats; luxA-E is the re-engineered lux cassette; (see Example 3); "kanamycin" is the kanamycin resistance gene; "Tranposase Tn4001" is the gene encoding the transposase enzyme of the same denomination.

In the construct shown in FIG. 3 the transposase gene (tnp) is located within the transposable unit. In an alternative construction the transposase gene may be deleted from the transposon itself and placed on the vector backbone. For example, in the vector shown in FIG. 1 the transposase might be introduced into the vector backbone at a unique restriction site in the multiple cloning site (MCS) region.

B. Construction of the pSK Tn4001 luxABCDE km$^R$ pE194 Shuttle Vector

As an alternative to using pAUL-A as a delivery system for the Tn4001 luxABCDE construct, the plasmids pSK and pE194 were used in combination.

The Tn4001 cassette was moved from pMGC57 into pSK as follows: The Tn4001 cassette was cut from pMGC57 using XhoI/PstI and ligated with similarly cut pSK. This ligation was electroporated into competent *E. coli* DH5α and transformants selected on LB containing 100 µg/ml ampicillin, IPTG, X-gal. White colonies were screened by PCR using the primers M13R and TNP-R2 (sequence in Tn4001 transposase gene). Colonies indicated to be positive by PCR were plasmid prepped and these DNA's cut with XhoI/PstI to confirm that they contained the correct size fragment.

The luxABCDE km$^R$ cassette was then moved into pSK Tn4001 so that it lay between the two IR sequences. First, the ampicillin cassette was removed from pSK luxABCDE km$^R$ using the enzymes AhdI/KpnI (in order to aid subsequent cloning of the lux cassette into pSK Tn4001). The luxABCDE km$^R$ cassette was then excised from the ampicillin deleted pSK backbone with BamHI/XhoI. The pSK Tn4001 DNA was then cut with EcoRV and ligated with the blunt-ended luxABCDE km$^R$ cassette.

The ligation was electroporated into competent *E. coli* DH5α and transformants selected on LB containing 100 µg/ml ampicillin. Light transformants were patched on either chloramphenicol or kanamycin. The correct orientation of the positive clones was confirmed by PCR using the primers M13F and LuxA-R.

Next, pSK Tn4001 luxABCDE km$^R$ was linearized with SacI and blunt-ended. Finally, this DNA was then ligated with blunt-ended ClaI-cut pE194, resulting in the pSK Tn4001 luxABCDE km$^R$ pE194 shuttle vector construct.

This construct was electroporated into competent *E. coli* DH5α. Transformants were selected on LB containing 150 µg/ml erythromycin. Resulting light colonies were then patched onto LB containing 100 µg/ml ampicillin and LB containing either 50 µg/ml kanamycin or 15 µg/ml chloramphenicol.

Testing transposition of pSK Tn4001 luxABCDE km$^R$ pE194: the plasmid was electroporated into *S. aureus* RN4220 and transformants selected on chocolate plates containing 0.3 µg/ml erythromycin. Approximately 50 of the resulting colonies were patched onto chocolate plates containing 0.3 µg/ml erythromycin, before being streaked onto BHI plates containing 200 µg/ml kanamycin.

20 of the 50 transformants (RN4220 pSK Tn4001 luxABCDE km$^R$ pE194) gave large numbers of clearly definable colonies that produced light (approximately 10% light colonies on average). Plasmid DNA was purified from two RN4220 transformants, and this DNA was electroporated into *S. aureus* 8325-4. The transformants were selected for on chocolate plates containing 0.3 µg/ml erythromycin using the same procedure employed for *S. aureus* RN4220.

*S. aureus* 8325-4 pSK Tn4001 luxABCDE km$^R$ pE194 transformants patched onto BHI containing 200 µg/ml kanamycin resulted in 50% of the transformants giving a large number of clearly definable colonies that produced light (approximately 10% light colonies on average).

C. Construction of the pE194 Tn4001 pSK luxABCDE km$^R$ Shuttle Vector

A Tn4001 luxABCDE km$^R$ shuttle vector was constructed wherein the Gram-negative origin was located inside of the two IR sequences. Firstly, the Gram-negative Tn4001 containing plasmid pMGC57 was fused with the Gram-positive erythromycin resistance plasmid pE194. pMGC57 was cut with PstI/BamHI and blunt-ended. At the same time pE194 was cut with ClaI and blunt-ended. These two linearized plasmids were then ligated and this mix was electroporated into competent *E. coli* DH5α and transformants selected on LB containing 150 µg/ml erythromycin.

Secondly, the chloramphenicol resistance cassette and the Gram-negative origin were removed from the pMGC57/pE194 composite. Plasmid DNA purified from a number of above erythromycin resistant colonies was cut with KpnI/XhoI (sites flanking the chloramphenicol resistance cassette and the Gram-negative origin) and a proportion of each digest was run on an agarose gel to identify a plasmid of the correct size. The remainder of a plasmid digest appearing to be the correct size was then blunt-ended and ligated. This ligation was electroporated into *S. aureus* RN4220 and plated onto chocolate agar containing 0.3 µg/ml erythromycin.

Finally, the pSK luxABCDE km plasmid was introduced within the IR of Tn4001. Plasmid DNA purified from 10 of the pMGC57/pE194 ori cm$^R$ *S. aureus* clones was cut with EcoRV and a proportion of each digest was run on an agarose gel to identify a plasmid of the correct size. The remainder of a plasmid digest showing the correct size (approximately 6 kb, #10) was then ligated with blunt-ended BamH1 cut pSK luxABCDE km DNA. This ligation was electroporated into DH5α and transformants selected on LB containing 150 µg/ml erythromycin. Bioluminescent colonies were then patched in duplicate onto LB plates containing either 50 µg/ml kanamycin or 100 µg/ml ampicillin to confirm the activity of the latter antibiotic cassettes. Since the probability of pSK luxABCDE km ligating into the former plasmid in the correct orientation should be approximately 50%, it was decided that such variants could be selected by phenotype in *S. aureus* (only plasmids with lux in the correct orientation imparting bioluminescent upon transposition).

Testing transposition of pE194 Tn4001 pSK luxABCDE km$^R$: Plasmid DNA from 100 positive colonies (pooled) was purified and used to transform RN4220, selecting on chocolate agar containing 0.3 µg/ml erythromycin. Approximately 50 of the resulting colonies were patched onto chocolate plates containing 0.3 µg/ml erythromycin, before being streaked onto BHI containing 200 µg/ml kanamycin. Eight of the latter 50 transformants gave rise to single colonies on kanamycin, with only two of these giving bioluminescent colonies. The latter plasmids were designated pE 194 Tn4001 pSK luxABCDE km$^R$ #1 and #8.

Plasmid DNA was purified from the two positive clones (from the original transformant grown on 0.3 µg/ml erythromycin) and this was used to transform *E. coli* and *S. aureus* RN4220 (again). Transformants of *E. coli* were selected on LB containing either 150 µg/ml erythromycin, 50 µg/ml kanamycin or 100 µg/ml ampicillin. Although numerous transformants could be recovered on both erythromycin and kanamycin plates, none could be recovered on plates containing ampicillin, indicating the plasmid to have rearranged.

Fifty RN4220 transformants of pE194 Tn4001 pSK luxABCDE km$^R$ #1 were gained on chocolate plates containing 0.3 µg/ml erythromycin. These transformants were patched onto chocolate plates containing 0.3 µg/ml erythromycin and then streaked onto BHI containing 200 µg/ml kanamycin. Two transformants (designated 1–43 and 1–46) were found to give a higher proportion of light colonies (approximately 50%).

Plasmid DNA was purified from these two RN4220 transformants, and this was electroporated into 8325-4, selecting for transformants on chocolate plates containing 0.3 µg/ml erythromycin. Again the transformants were patched onto chocolate plates containing 0.3 µg/ml erythromycin and then streaked onto BHI containing 200 µg/ml kanamycin.

More than half of the transformants gave a large number of clearly definable colonies that produced light (approximately 10% light colonies on average). One such transformant (1–46E) was found to give approximately 50% light colonies when streaked onto BHI containing 200 µg/ml kanamycin.

Recovery of this plasmid type (pE194 Tn4001 pSK luxABCDE km$^R$) from either RN4220 or 8325-4 varied from no recovery to 20 µg/liter. Furthermore, experiments performed in support of the current invention indicated that it was not possible to gain transformants in *E. coli* by electroporating re-ligated chromosomal DNA (cut individually with a wide range of restriction enzymes) from bioluminescent strains of *S. aureus* and selecting on LB containing 50 µg/ml kanamycin.

EXAMPLE 6

Preparation and Selection of Constitutively Bioluminescent Gram-Positive Bacteria Using the Gram-Positive lux Transposon Tn4001 luxABCDE km$^R$ pAUL-A IR luxABCDE km$^R$ tnp IR shuttle vector DNA was isolated from *S. aureus* 8325-4 transformants (Example 5, above) that had been shown to give stable, light-generating transformants after selection on kanamycin. This DNA (from *S. aureus* 8325-4 transformants designated 16, 19, 20, 23, 26) was electroporated into competent cells of *S. aureus* RN4220 and RN6390, *S. pneumoniae* D39, and *L. monocytogenes* (ATCC 23074). Transformants of these strains were obtained on chocolate agar containing 0.3 µg/ml erythromycin.

Several colonies of *S. aureus*, *S. pneumoniae* and *L. monocytogene* were identified that constitutively produced light at levels which appeared to be sufficient to allow the organisms to be seen in animals using in vivo imaging. Several of these bacterial clones were selected, and their in vivo bioluminescence levels were tested as described below in Example 8.

EXAMPLE 7

Isolation of Heat-Shock Protein Promoters from Gram-Positive Organisms Using the IR luxABCDE km$^R$ tnp IR Construct

Figure 4:
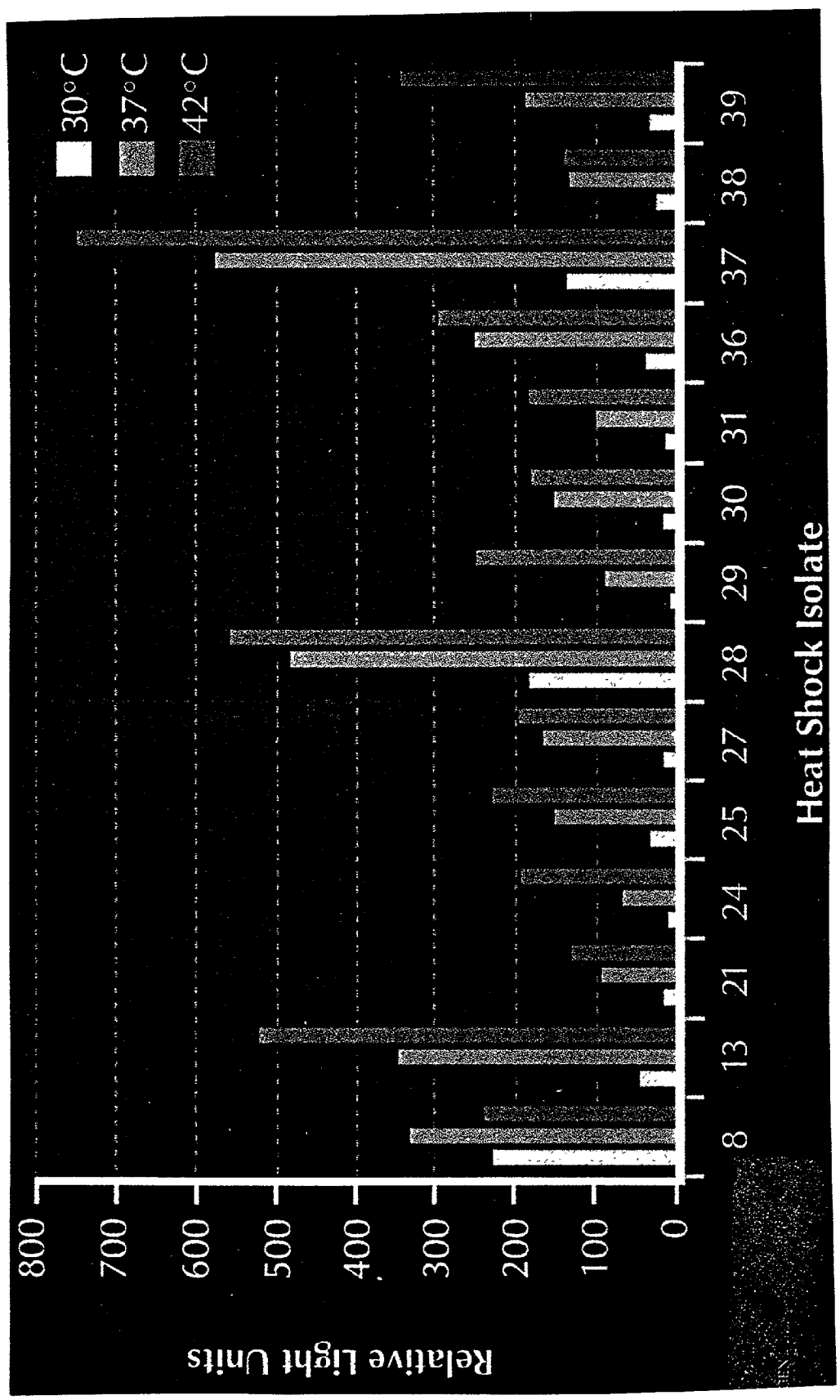
FIG. 4 presents data showing relative light unit expression from a variety of heat shock isolates constructed by the methods of the present invention.

*L. monocytogenes* was screened for transformants where expression of KanR and light production were heat inducible. One milliliter of an overnight culture grown at 30° C. of *L. monocytogenes* transformed with pAUL-A IR luxABCDE km$^R$ tnp IR was inoculated into 30 ml of Brain Heart Infusion (Gibco BRL, Gaithersburg, Md.) containing 200 µg/ml kanamycin. This culture was then incubated overnight at 42° C., centrifuged, and the cell pellet resuspended and plated for single colonies on BHI plates containing 200 µg/ml kanamycin. These plates were incubated at 42° C. and then screened for light-generating colonies. Light-generating colonies were patched onto two blank BHI plates (i.e., plates containing no kanamycin). One set of plates were incubated at 30° C. and the other set at 42° C. Comparison of the patches for bioluminescence at the two temperatures, revealed a number of isolates that were strongly induced for light production at 42° C. Some representative data for such isolates were presented in FIG. 4. In the figure, the X-axis shows a number of bacterial isolates and the Y-axis shows relative light units (RLU) for each bacterial isolate, cultures of which were grown at three temperatures (30° C., 37° C., and 42° C.). As can be seen from the data presented in the figure, light production in the isolates can be induced to various degrees by temperature, and ranges from being mildly temperature conditional to strongly temperature conditional.

These data suggest that the IR luxABCDE km$^R$ tnp IR vector constructs of the present invention can be used to identify conditional promoters in gram-positive bacteria.

EXAMPLE 8

Measuring in vivo Levels of Bioluminescence in Mice of Strains of *Staphylococcus aureus*, *Staphylococcus pneumoniae* and *Listeria monocytogenes* Carrying the IR luxABCDE km$^R$ tnp IR Construct The ability to effectively monitor in real time bioluminescent bacteria in living animals was demonstrated using mice infected with isolates of bioluminescent transformed *S. aureus* 8325-4, *S. pneumoniae* D39, and *L. monocytogenes* 23074.

Exponential cultures of the aforementioned bacteria carrying the Tn4001 cassette of the present invention were grown at 37° C. in growth media containing a selection agent, pelleted and then resuspended in phosphate-buffered saline (PBS). Bacterial concentrations were estimated spectrophotometrically by absorbance at 600 nm and adjusted to an appropriate concentration by dilution with PBS. The cells were then held on ice for a short period until the mice were ready to be inoculated. Cell numbers were verified by plating dilutions of inoculum onto agar containing the appropriate growth medium.

Mice were anesthetized with ketamine (100 mg/ml) and xylazine (20 mg/ml), mixed at a 4:1 ratio v/v just before use.

100 mg of ketamine/xylazine mixture (dose based on ketamine concentration) per kg body weight was injected intramuscularly into the right hamstring muscle. After anesthesia was established, the mice were injected in the left anterior tibialis with the bacterial inoculum. Mice were imaged at 0, 4, 8, and 24 hours post-infection using a CCD camera. At each time point, both dorsal and ventral images were taken. All images were collected for 5 minutes.

Total photon emission from selected and defined areas within the images of each mouse were then quantified using the LivingImage software package (Xenogen Corporation, Alameda, Calif.). The photon signal from the anterior tibialis muscle was quantified from the dorsal and ventral images of each mouse, and a dorsal-ventral average was calculated. This averaging corrects for light scattering differences due to mouse-to-mouse variation in the tissue depth of the bacteria.

Isolates obtained by the methods of the present invention were tested (a total of 12 S. aureus 8325-4 isolates; 3 S. pneumoniae D39 isolates; and 2 L. monocytogenes isolates). All gave bioluminescence levels that were detectable in vivo, thereby demonstrating that bioluminescent bacteria can be effectively monitored in living animals in real time.

After the 24 h imaging time point, mice were sacrificed and the infected thigh muscles (both the anterior tibialis and the quadricep muscle) were surgically removed. The muscle tissue was homogenized in 500 μl PBS using a loose Dounce Homogenizer. The tissue and bacterial suspension was then diluted in PBS by $10^5$, $10^6$, and $10^7$ to a final volume of 1 ml for each dilution. 100 μl of each dilution was plated out in duplicate onto media plates and incubated overnight at 37° C. The following morning, colonies were counted and the numbers of CFU for each tissue sample were estimated.

Extraction of bacteria from the thigh muscles of each of the mice demonstrated that pathogenic bacterial strains modified with the transposon cassette of the present invention can effect a stable infection. Further, these experiments confirmed that bioluminescent data provides an accurate prediction of the number of viable bacteria present in the tissue.

EXAMPLE 9

Identification of Genes Specifically Involved in the Pathogenesis of Gram-Positive Bacteria Using In Vivo Expression Technology The regulation of both the lux and the kanamycin resistance genes in the IR luxABCDE $km^R$ tnp IR vector constructs of the present invention are tightly coupled, owing to their close physical association in the luxABCDE $km^R$ cassette. Accordingly, the constructs of the present invention can be used to identify genes specifically involved in the pathogenicity of Gram-positive bacteria using the following in vivo expression technology (IVET) protocols.

A pathogenic strain of gram positive bacteria, for example, S. aureus, is transformed with an IR luxABCDE $km^R$ tnp IR vector construct of the present invention. The transformed strain is grown under conditions to maintain the shuttle vector construct, for example, under conditions which select for erythromycin resistance when using the pAUL-A IR luxABCDE $km^R$ tnp IR construct.

An experimental animal, such as a mouse, is injected with the transformed bacteria; shortly thereafter, the animal is injected with kanamycin to select for bacteria that have acquired kanamycin resistance. This step selects for transposants which have integrated the IR luxABCDE $km^R$ tnp IR cassette next to active bacterial promoters.

These KanR bacteria are extracted from the animal and plated onto non-selective media, and dark colonies are selected. This step selects for integrants located adjacent to or near bacterial promoters that are not constitutively active. The dark colonies are then cultured and injected into experimental animals, which are monitored for bacterially-mediated light production. Induction of light production in vivo in these isolates suggests the identification of a bacteria promoter turned on in response to infection of its mammalian host (i.e., a promoter involved in establishment of infection).

Likewise promoters active at other stages in pathogenicity and/or life cycle of a light-generating microorganism, obtained by the methods of the present invention, can be similarly evaluated. For example, bacterial genes active during chronic infection but not active during the establishment of infection may be identified by comparing in vivo light production during early stages of infection versus in vivo light production during chronic infection.

For example, a first animal is infected with pathogenic bacteria transformed with a shuttle vector construct of the present invention, for example, the pAUL-A luxABCDE $km^R$ shuttle vector described above. After the infection is allowed to become established, the animal is then treated with a selective agent, e.g., kanamycin. This step selects for transposants wherein the expression of bioluminescence and antibiotic resistance is controlled by a promoter active either constitutively or during the chronic stages of infection (vs. during the initial stages). Bacteria are then extracted and replica-plated onto selective and non-selective media. Dark, non-resistant colonies (constituting transposants wherein the promoter is not constitutively produced, but is active only during the chronic stages of infection) are selected, and used to infect a second animal. The second animal is then monitored for light induction.

In this way, expression of the genes specifically induced during different stages of pathogenesis and/or specific stages of the life cycle of a light-generating bacteria (made by the methods of the present invention) may be monitored in vivo. Specific tagging of promoters of such genes also allows for the screening of compounds which interfere with that particular stage of bacterial pathogenicity or life cycle.

EXAMPLE 10

Identification and Isolation of Gene Promoters

Bacteria are isolated from experimental animals that exhibit bioluminescence attributable to the activity of either constitutive, repressible or inducible promoters. The promoters are then identified and/or isolated by a number of methods which are well known in the art.

Promoters associated with known genes in the target organism may be identified by genetic mapping techniques. For example, the genomic location of the integrated luxABCDE $km^R$ cassette is mapped and the map position compared to the known genetic map of the organism to identify the gene at the corresponding position. Such mapping is carried out by standard genetic methods known in the art. To exemplify, an apparently constitutively expressed luxABCDE $km^R$ cassette is mapped to the physical genomic location known to correspond to the gene encoding glucose-6-phosphate dehydrogenase. The expression of the luxABCDE $km^R$ cassette is, therefore, likely mediated by the glucose-6-phosphate dehydrogenase promoter.

Alternatively, PCR amplification of the promoter and subsequent sequencing of the amplification products may be employed. The luxABCDE km$^R$ cassette in the bioluminescent transposants of interest integrates adjacent or in close proximity to active bacterial promoters. PCR primers based on DNA sequences present in the integrated lux ABCDE km$^R$ cassette, for example, the kanamycin resistance gene, can be used in amplification reactions to take advantage of the close proximity of the unknown promoter sequence to the known nucleic acid sequence. Sequencing from known sequences into the associated bacterial sequences reveals the sequence of the promoter.

The technique of inverse PCR may also be used. For example, genomic DNA from each of the heat shock inducible strains (HS) obtained in Example 7 above was cut with the four-base recognition restriction enzyme AluI (AG/CT), ligated for 4 hours at RT, and inverse PCR performed using the primers LuxIF3 (GCT TGG TAA CCC TTA TGT CGC) (SEQ ID NO:16) and LuxR3 (GGG AGG TTG GTA TGT AAG C) (SEQ ID NO:17). Cloning and sequencing of the resulting PCR products confirmed HS1 and 2 to have the Tn4001 luxABCDE km$^R$ cassettes fused within a single gene of unknown function.

A promoter may also be sequenced by directly isolating chromosomal DNA from a single bioluminescent bacterial colony of interest, and then sequencing the DNA using primers specific for regions of the kanamycin resistance gene adjacent or in close proximity to the promoter sequence of interest.

For example, this last approach was used to identify the genes into which the Tn4001 luxABCDE km$^R$ cassettes had transposed in the various *L. monocytogenes* heat shock (HS) strains obtained in Example 7 above.

Genomic DNA was isolated from *L. monocytogenes* HS 1-HS39. This DNA was then cut individually with a number of different restriction enzymes, ligated into pBluescript SK$^-$ and then electroporated into *E. coli* DH5α.

When cloning the luxAB genes, the enzyme EcoRV (unique site directly downstream of luxB) was used in combination with one other enzyme found in the MCS of pSK (i.e., SacI, XbaI, EcoRI, SalI, XhoI or KpnI). In the case of cloning the km$^R$ gene, the enzymes AfeI (blunt) or HindIII was used in combination with the same pSK MCS enzymes listed above. In either case (luxAB genes or km$^R$ gene), pSK was cut with SmaI and the same enzyme as that listed above prior to ligation.

Clones containing plasmid DNA with regions of the Tn4001 luxABCDE km$^R$ cassettes were selected by either screening for bioluminescence in the presence of exogenous aldehyde (indicating the presence of the luxAB genes from the 5' end of the cassette) or kanamycin resistance (indicating the presence of the km$^R$ gene from the 3' end of the cassette).

DNA from HS36 and 13 both gave light clones. DNA from HS27, 29, and 31 gave clones which exhibited kanamycin resistance. Plasmid DNA from these clones was sequenced by conventional methods and the sequences obtained were then compared with known sequences as a means of identifying the promoter region with which the luxA or km$^R$ coding sequence was associated.

HS 36 appears to have the Tn4001 luxABCDE km$^R$ cassette fused in a region of the *L. monocytogenes* chromosome involved with the regulation of hly expression. Interestingly, hly is also temperature regulated and is involved in *Listeria* pathogenicity.

HS 13 has the Tn4001 luxABCDE km$^R$ cassette fused at the 3' end of a hisH homolog. Heat induction of this gene has not been reported before. However, in *S. typhimurium* constitutive expression of histidine operon causes growth inhibition (Fink et al. 1967. J. Mol. Biol. 30:81–95; Flores and Casadesus, 1995. J. Bacteriol. 177:4841–4850) suggesting that expression of the genes in the operon can be regulated.

EXAMPLE 11

Identification of Effective Pharmacological Agents and Determination of their Point of Action A wide variety of pathogenic bacteria of interest may be modified to carry the IR luxABCDE km$^R$ IR construct, and the promoters induced during pathogenesis may be identified and isolated as described above in Examples 9 and 10. For a given organism, a panel of transformed cells representing a spectrum of promoters mediating pathogenesis may then be employed as a means for screening potential pharmacological agents, and simultaneously determining a particular agent's point of action.

Multiple groups of experimental animals (cohorts), each cohort corresponding to a particular gene of interest, are infected with the appropriate bacterial integrants and are then treated with the pharmaceutical agent of interest. Both the experimental animals and infected, untreated controls are then monitored for bioluminescence. In the case of effective agents, no bioluminescence is detected in the experimental animal, in contrast to the bioluminescence observed in the corresponding controls.

Similarly, the Tn4001 luxABCDE km$^R$ constructs of the present invention may be employed in order to identify novel antibiotics.

Multi-drug resistant Gram-positive bacteria, such as *Staphylococcus, Streptococcus, Enterococcus* and *Mycobacterium*, have increased dramatically over the past decade. Therefore, the development of methodologies aimed at identifying novel compound with which to combat these pathogens is vital. Conventional technologies for assessing the bactericidal/bacteristatic activity of a drug (i.e., plating/growth assays), while available, are extremely laborious and usually require 24–48 hrs for completion. Furthermore, such assays are of limited use for high-throughput screening and "follow-up" studies in the animal model.

The Tn4001 luxABCDE constructs of the present invention allow bacterial genes involved with drug resistance, in particular those in Gram-positive bacteria, to be tagged, identified and monitored both in vitro and in vivo. An example of how this technology may be applied to identify novel antibiotics follows.

*S. aureus* containing a promoterless plasmid-based Tn4001::luxA-E kan transposon cassette is cultured on solid non-selective media overnight at 37° C.

The culture is then overlain with minimum inhibitory concentrations ("MIC") of different classes of characterized antibiotics (e.g., gentamycin, penicillin etc), in order to induce operons which encode proteins conferring resistance to those antibiotics. The cultures of induced organisms are subsequently overlain with kanamycin to select for organisms wherein the transposon cassettes have integrated behind active promoters, and which are therefore expressing kanamycin resistance. Some of those organisms selected will have the transpsoson cassette integrated behind promoters associated with the antibiotic resistance genes induced by the initial antibiotic treatment.

The treated bacteria are plated on non-selective media and colonies that do not produce light (dark colonies) are selected. These colonies should be lux fusions downstream of an antibiotic-induced gene. (Such colonies represent antibiotic-detector strains). The ability of the pure cultures of a particular *S. aureus* fusion (dark colonies) to be induced ('light-up') when subjected to a MIC of a prior tested class of antibiotic is confirmed by re-treating with that drug.

To identify novel compounds, pure cultures of an antibiotic detector strain are exposed to different dilutions of novel compounds suspected of being antibiotics. Those compounds with analogous activity to the antibiotic to which the fusion was originally isolated will cause the fusion to 'light-up'

After confirming that the tested compound is bactericidal/ bacteristatic, its efficacy can be tested in animals using both the antibiotic detector strain and different constitutive light strains.

Although a particular drug may be of limited use against the parental detector strain, such an approach should identify compound that are effective against other bacteria, and visa versa.

EXAMPLE 12

Titration of Promoter Strength

The relative strength of promoters which have become operably linked to the lux $km^R$ cassette via integration may be determined by replica plating of the transposants onto culture medium of increasing kanamycin concentration. Alternately, the strength of the promoter may be determined by growing the cells in liquid media where individual liquid cultures contain serial dilutions of the antibiotic. Comparison of the degree of colony growth, and/or the relative intensity of bioluminescence, over increasing antibiotic concentrations, provides an indication of the relative strength of promoter activity.

Also, a curve of promoter strengths is established using, for example, integrated luxABCDE $km^R$ cassette integrated next to (i) a relatively weak promoter from a gene expressed at low levels, (ii) a house keeping gene promoter, (iii) a highly active promoter, all integrants in the target organism. A bioluminescence curve is established for these integrants where bioluminescence is evaluated for the same number of cells, under the same growth conditions. Comparisons of bioluminescence mediated by promoters in the same target organism is then evaluated by measuring bioluminescence using the same number of cells under the same growth conditions used to establish the curve. This provides a measure of the relative strength of the promoter that is mediating expression of the light-generating polypeptide.

EXAMPLE 13

High-Density Screening of Bioluminescent Transposants

As an alternative to the use of selective media, bioluminescent colonies were isolated from among colonies plated at high density on solid medium using optical detection and manual selection.

*S. aureus* 8325-4 cells were transformed with pE194 Tn40001 luxABCDE, plated on solid non-selective media plates at a density of $10^4$ to $10^5$ cells per plate, and grown overnight at 37° C. Strongly bioluminescent single colonies were detected using an ICCD camera, and those colonies were selected using a disposable micropipette tip; selection of the desired colony was confirmed using the camera. The selected colony was used to inoculate a volume of liquid growth medium, which was then streaked onto fresh media plates. The plates were incubated overnight at 37° C. The process was repeated until isolation of a pure colony was confirmed by observation of essentially uniform light intensity among single colonies on the streaked plates.

The preceding demonstrates a method that avoids the need for an antibiotic selection as a means of isolating organisms of interest transformed with the transposon cassettes of the present invention.

EXAMPLE 14

Visualizing Pneumococcal Infections in the Lungs of Living Mice Using Bioluminescent *Streptococcus pneumoniae* Transformed with a Novel Gram-Positive lux Transposon

*Streptococcus pneumoniae* is the leading cause of invasive bacterial disease in the very young and the elderly, and is the bacterium most responsible for community-acquired pneumonia in the developed world (Schuchat et al 1997). In the United States pneumococci cause up to 40,000 deaths annually, primarily among the elderly (CDC 1989, 1995). In the developing world they are an important cause of childhood deaths due to secondary respiratory infection following viral disease, killing an estimated one million children annually (Greenwood, 1999; Briles et al. 2000).

*S. pneumoniae* can behave as a transient commensal, colonizing the mucosal epithelium of the nasopharynx of 40% of healthy adults and children, with no adverse effects (Austrian, 1986). Children carry this pathogen in the nasopharynx asymptomatically for about 4 to 6 weeks, often carrying several serotypes at a time (Gray and Dillon, 1986; Tuomanen et al. 1995). Having acquired serotype-specific immunity, they go on to acquire a new serotype every 2 months or so. Occasionally, perhaps in conjunction with a viral infection, one of these strains gives rise to a symptomatic pneumococcal infection including sinusitis, otitis media, and pneumonia. In rare cases sepsis develops, especially in patients infected with the human immunodeficiency virus (Farley et al. 1994), and seeds infections at distant sites causing meningitis (Hwang et al. 2000). By the age of 5 years, the majority of children in the United States will have experienced at least one case of pneumococcal otitis media. It is estimated that 25% of all community-acquired pneumonia is due to pneumococcus. While the incidence of meningitis is far less (1 in 100,000 per annum), pneumococcal meningitis has a 25% mortality rate, which is higher than that of other meningeal pathogens (Schuchat et al. 1997). Moreover, 50% of the survivors sustain permanent neurological sequelae (Khoosheh and Tuomanen, 2000).

Although pneumococcal vaccines can be extremely effective, a lack of broad range coverage makes them of limited use in preventative treatments, especially the use of polysaccharide vaccines in infants and children under 2 years of age (Lee and Wang, 1994). Treatment of established pneumococcal infections has also worsened in resent years with the increased occurrence of multidrug resistant strains of *S. pneumoniae*. About one-third to one-half of pneumococci recovered from humans have become at least partially resistant to penicillin, which may occur in addition to resistance to a number of other common antibiotics (Appelbaum, 1992; Briles et al. 2000). The rise of antibiotic resistance among pneumococci has already complicated treatment, especially of meningitis, and threatens to greatly increase the morbidity and mortality caused by pneumococci unless new control measures are developed (Briles et al. 2000). These factors, plus the ability of pneumococcus to transfer genes for resistance, capsule, and virulence via transformation (Khoosheh and Tuomanen, 2000), make it imperative to develop a better understanding of the mechanism by which pneumococcus causes disease.

To this end, a Gram-positive lux transposon, Tn4001 luxABCDE km$^R$ (described above) was used to generate bioluminescent strains of *S. pneumoniae*. Furthermore, using a pneumococcal lung model, the advantage of using these bioluminescent strains to study *S. pneumoniae* disease in living animals was demonstrated.

Figure 5:
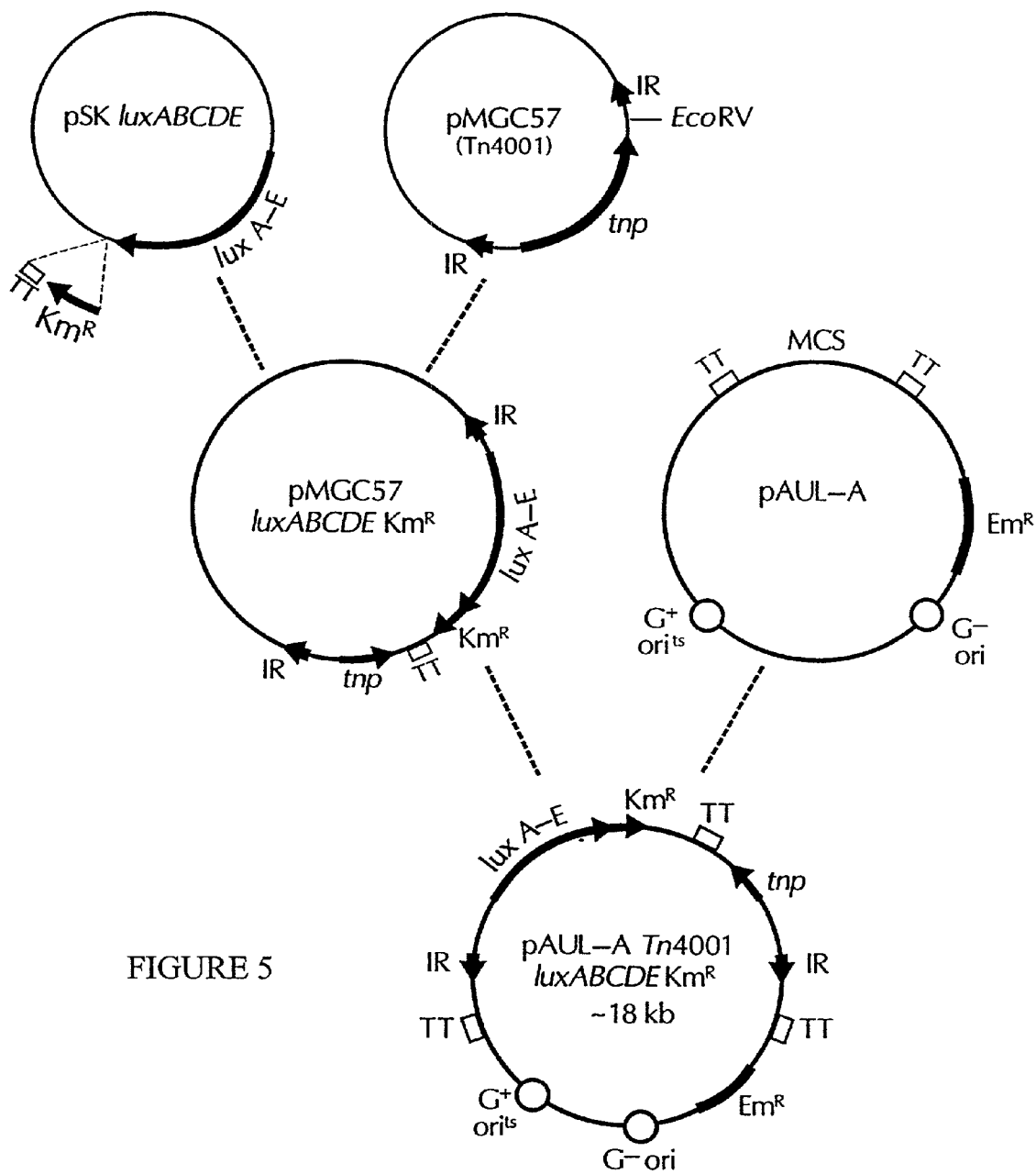
FIG. 5 depicts construction of the plasmid pAUL-A Tn4001 luxABCDE $Km^R$. (See, Example 14). "IR" refers to inverted repeat; "$Km^R$" refers ti kanamycin resistant gene; "$Em^R$" refers to erythromycin resistant gene; "tnp" refers to transposase gene; "TT" refers to transcription terminator; and "MCS" refers to multiple cloning site.

Construction of the Gram-positive lux transposon plasmid, pAUL-A Tn4001 luxABCDE km$^R$. Construction of the plasmid pAUL-A Tn4001 luxABCDE km$^R$ is shown schematically in FIG. 5. Briefly, a *Photorhabdus luminescens* lux operon, previously altered to be functional in Gram-positive bacteria as described herein, was modified by linking a promoterless Gram-positive kanamycin resistance cassette downstream of luxE. The kanamycin resistance gene was PCR amplified from pDL289 (Buckley et al. (1995) *J. Bacteriol* 177:5028–5034) using the primers KanF2-5' CTG TAG ACT CGA GGA GGG AAA TAA TAA ATG GC 3' (SEQ ID NO:12) and KanR2-5' CAG AGT GTC GAC AGT TGC GGA TGT AC 3' (SEQ ID NO:13) (underlined sequences correspond to XhoI and SalI restriction enzyme sites, respectively, which were introduced to help clone this gene). PCR conditions for this and subsequent DNA amplifications were as those previously described herein.

The amplified kanamycin resistance gene was digested with XhoI and SalI, and ligated into the SalI site of pBluescript II SK$^-$ luxABCDE (see, above). The ligation was electroporated into *E. coli*, spread onto Luria-Bertani (LB) agar containing 50 µg/ml kanamycin, and incubated overnight at 37° C. Plates with kanamycin resistant colonies were screening for bioluminescence using a photon counting intensified charged couple device (ICCD) camera (model 2400-32, Hamamatsu Photonics, Bridgewater, N.J.). Plasmid DNA was isolated from bioluminescent, kanamycin resistant colonies using a standard alkaline lysis procedure (Plasmid Spin Miniprep Kit, Qiagen, Valencia, Calif.), as were all subsequent plasmid isolations. These plasmids were then screened by PCR using the primers KanF2 and M13F-5' GTA AAA CGA CGG CCA GT 3' (SEQ ID NO:19) (flanking the multiple cloning site of pBluescript II SK$^-$), to identify constructs where the luxABCDE cassette was in the same orientation (5' to 3') as the kanamycin resistance gene.

A Gram-positive lux transposon was constructed as described in Examples 4 and, to increase the efficiency of transposition in Gram-positive bacteria, was moved onto the temperature sensitive Gram-positive/negative shuttle vector pAUL-A (Chakraborty et al. (1992) *J. Bacteriol*. 174:568–574) as described in Example 5.

Both lux and km$^R$ genes are silent on pAUL-A in *S. pneumoniae*. Although the luxABCDE km$^R$ operon inserted in pAUL-A is flanked on both sides by strong transcriptional terminator sequences (FIG. 5), which should act to silence gene expression (Chakraborty et al. 1992, supra), regulation of this plasmid bound operon is different between *E. coli* and *S. pneumoniae*.

*E. coli* (DH5α, Life Technologies, Rockvill, Md.) transformed with pAUL-A Tn4001 luxABCDE km$^R$ were uniformly bioluminescent, kanamycin resistant and erythromycin resistant (100% of all transformants initially selected on erythromycin). Since the transformation frequency of these cells was similar to that of *E. coli* transformed with the empty pAUL-A plasmid (approximately 500 CFU/µg DNA), and pAUL-A Tn4001 luxABCDE km$^R$ DNA could be readily extracted from the transformants using standard plasmid isolation procedures, it is unlikely that lux km$^R$ gene expression is due to integration of the plasmid into the *E. coli* chromosome (i.e., episomal). Without being bound by any theory, it is possible that the luxABCDE km$^R$ operon is expressed on pAUL-A in *E. coli*, despite the lack of any apparent promoter upstream of these genes.

In contrast to that found in *E. coli*, in *S. pneumoniae* the plasmid based luxABCDE km$^R$ operon was silent. Electrocompetent cells of *S. pneumoniae* strain D39 (obtained from Tom Parr, Eli Lilly, Indianapolis, Ind.) were prepared by inoculating a single colony of this bacterium in 10 ml of Todd-Hewitt broth supplemented with 0.2% yeast extract (THY) and incubating at 37° C. and 5% $CO_2$. The overnight culture was diluted 1:100 in THY containing 20 mM glycine and incubated until the optical density ($OD_{600}$) was 0.3. After centrifugation, the pellet was resuspended in 30 ml of supernatant and competence stimulating peptide CSP1 (EM-RLSKFFRDFILQRKK) (SEQ ID NO:20) (Havarstein et al. (1995) *PNAS USA* 92:11140–11144) was added at a final concentration of 100 ng/ml. The bacteria were heat shocked at 42° C. for 10 minutes and the competent cells were harvested by centrifugation. The pellet was washed with 30 ml of ice-cold 0.5 M sucrose, followed by a wash with 30 ml of ice-cold 10% glycerol. The pellet was then resuspended in 10% glycerol (1/100 volume of original culture). Aliquots were stored at −80° C.

For electroporation, 1 µg of pAUL-A Tn4001 luxABCDE km$^R$ DNA was mixed with 50 µl of competent cells on ice. The mixture was transferred to a 0.2 cm cuvette and electroporated using Bio-Rad GenePulser II (Hercules, Calif.) at 17.5 kV/cm, 25 µF capacitance and 400 Ω resistance. Immediately following electroporation, 1 ml of ice-cold THY medium was added. The bacteria were kept on ice for 10 minutes and then incubated for 4 hours at 37° C. and 5% $CO_2$. The transformation mix was plated on chocolate agar containing 0.3 µg/ml of erythromycin and the plates were incubated for 24 to 48 hr.

Transformants of *S. pneumoniae* D39 containing the plasmid pAUL-A Tn4001 luxABCDE km$^R$ were patched onto chocolate agar plates containing 0.3 µg/ml erythromycin and incubated overnight. A quantity of each patch (10 µl loop-full of cell growth consisting of approximately $10^8$–$10^9$ cells) was then uniformly streaked over the entire area of a chocolate agar plate containing 400 µg/ml kanamycin and incubated for 24 to 48 hrs. Alternatively, *S. pneumoniae* D39 pAUL-A Tn4001 luxABCDE km$^R$ was cultured overnight in 10 ml Brain Heart Infusion (BHI) containing 0.3 µg/ml erythromycin, pelleted, re-suspended in an equal volume of BHI, and 100 µl volumes of a 10-fold dilution range ($10^0$–$10^{-8}$ in BHI) spread onto chocolate agar plate containing 400 µg/ml kanamycin and incubated for 24 to 48 hrs. The resulting colonies were screened for bioluminescence using an ICCD camera and the brightest were streaked onto chocolate agar plates containing 400 µg/ml kanamycin. Single colonies were re-streaked several times onto chocolate plates containing no antibiotics to verify that bioluminescence was stable in the absence of antibiotic selection. Each transposant was then graded for its level of bioluminescence using an ICCD camera and Xenogen's LivingImage™ software (Xenogen Corporation, Alameda, Calif.).

*S. pneumoniae* transformants containing pAUL-A Tn4001 luxABCDE km$^R$ were dark when selected on chocolate plates containing 0.3 µg/ml erythromycin. Furthermore, the growth rate of an exponentially dividing culture of such a transformant was dramatically inhibited by the addition of kanamycin at concentrations of 400 µg/ml and higher. However, once growth of the culture had reestablished after several hours in the presence of kanamycin, its rate was similar to that found prior to the addition of this antibiotic. Moreover, a low level of bioluminescence could be recorded form the latter culture, indicating that a subpopulation of the original culture, one in which the luxABCDE km$^R$ operon had been induced, had been selected for.

Figure 6:
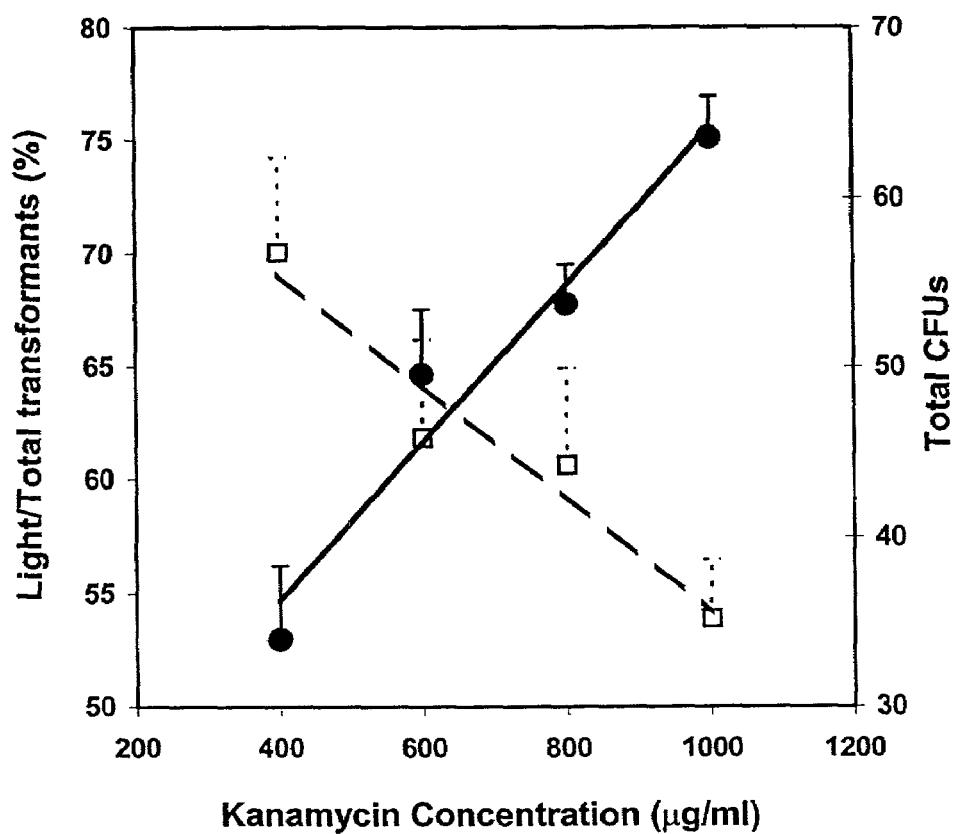
FIG. 6 is a graph depicting the effects of kanamycin concentration on the selection of promoter strength. S. pneumoniae strain Xen 7 was grown to mid exponential phase and $10^3$ CFUs were plated on chocolate agar plates supplemented with varying concentration of kanamycin. Open squares (□) represent the total CFUs on the plates. Solid circles (●) represent the ratio of light vs total CFUs. The numbers of CFUs were the average of 5 plates at each kanamycin concentration.

Promoter strength can be selected for by varying the kanamycin concentration in the medium during the isolation of chromosomal integrants. S. pneumoniae pAUL-A Tn4001 luxABCDE km$^R$ plated at 10$^3$ CFUs on chocolate agar plates containing increasing concentrations of kanamycin (400 to 1000 µg/ml), gave decreasing numbers of colonies (56 to 35, on average). In comparison, this same density of cells plated on chocolate plates without kanamycin, resulted in approximately 1000 CFUs. Although increasing the concentration of kanamycin in the medium gave rise to less transformants, the proportion of colonies producing higher levels of bioluminescence was found to increase (FIG. 6). This indicates that increasing the concentration of kanamycin in the medium results in the selection of fusions with stronger promoters upstream of the luxABCDE km$^R$ operon. Even in the absence of kanamycin selection (screening on blank chocolate plates), approximately 3% of the 1000 or so colonies were bioluminescent. This level of transposition seen in S. pneumoniae was significantly higher (approximately 3 orders of magnitude) than that observed in studies involving pAUL-A Tn4001 luxABCDE km$^R$ in *Staphylococcus aureus* and *Listeria monocytogenes*.

Tn4001 luxABCDE km$^R$ is randomly inserted into the chromosome of S. pneumoniae and is stably maintained. One thousand bioluminescent, kanamycin resistant S. pneumoniae D39 colonies were patched in duplicate onto chocolate plates containing either 0.3 µg/ml erythromycin or 400 µg/ml kanamycin. All but 20 colonies grew on both antibiotics, indicating that the vast majority (98%) of the integrants to be episomally based (whole plasmid integrated into the chromosome) as opposed to true transposants. Southern blot analysis of genomic DNA from 10 kanamycin/erythromycin resistant colonies, confirmed the entire pAUL-A Tn4001 luxABCDE km$^R$ construct to have integrated into the S. pneumoniae chromosome. In contrast, Southern blot analysis (conducted according to the manufacturer's instructions of Alkphos Direct Labeling Kit, Amerhsam Pharmacia Biotech, Piscataway, N.J. using a probe amplified with primers XAF (SEQ ID NO:2) and XAR (SEQ ID NO:3)) of genomic DNA from 10 kanamycin resistant/erythromycin sensitive colonies showed all ten isolates to be true transposants, and that each strain contained only one copy of the lux transposon construct.

Furthermore, inverse PCR was used to facilitate sequencing of the chromosomal lux fusion junctions. Briefly, the genomic DNA sequence lying upstream of each Tn4001 luxABCDE km$^R$ integration site was obtained using inverse PCR (Ochman et al. (1988) *Genetics* 120:621–623). Chromosomal DNA from S. pneumoniae Tn4001 luxABCDE km$^R$ was digested with a number of different restriction enzymes (both 4 and 6 base pair recognition enzymes) and self-ligated. The upstream region was PCR amplified using the primers R2-5' CGT TTC ATT ACC TCT GTT TGA G 3' (SEQ ID NO:18) and XBF-5' GGG AAT TCT CGA GGA GGA GAG AAA GAA ATG AAA TTT GGA 3' (SEQ ID NO:4). Resulting PCR products were purified (PCR purification kit; Qiagen, Valencia, Calif.) and directly sequenced using the primer R2. Sequencing of the chromosomal lux fusion junctions (gained by this inverse PCR) of each of these transposants confirmed all ten integration sites to be unique, confirming Tn4001 transposition in S. pneumoniae to occur randomly.

Four clinical isolates of S. pneumoniae were naturally transformed with chromosomal DNA of a highly bioluminescent, kanamycin resistant, erythromycin sensitive D39 transposant, designated Xen 7. The transformation efficiency varied from 50–500 CFUs/µg of Xen 7 chromosomal DNA. These transformants were named Xen 9, Xen 10, Xen 11 and Xen 12, corresponding to the strains HUSTMBIG, A66.1, EF3030 and 140301 (obtained from Marc Lipstich, Harvard School of Public Health, Boston, Mass. and David Briles, University of Alabama at Birmingham, Birmingham, Ala.), respectively. To test whether the transposon was stably maintained at its original integration site, Xen 9 and Xen 10 were cultured in BHI medium with the presence or absence of kanamycin for two weeks at 37° C., diluting the cells 1 in 1000 into fresh medium every 12 hrs. Chromosomal DNAs were prepared at day 0, 3, 7, 10 and 14, and the ratio of kanamycin resistant colonies vs. total CFUs was examined at the same times. Tn4001 luxABCDE km$^R$ in both Xen 9 and Xen 10 was found to be 100% stable, such that after 14 days of continuous culturing without antibiotic selection all CFUs were bioluminescent and the location of the transposons in both strains remained the same and at single copy.

Photon emission from bioluminescent S. pneumoniae decrease dramatically as cells entered stationary phase. To evaluate the level of bioluminescence seen from the different strains of S. pneumoniae during growth, relative light units (RLUs) were recorded from strain D39 (Xen 7) and the four clinical isolates (Xen 9-12) during in vitro growth using an ICCD camera and Xenogen's LivingImage™ software. Briefly, a single bioluminescent colony of S. pneumoniae was inoculated in 10 ml BHI medium. Three hundred microliters of overnight culture was inoculated in 30 ml BHI and grown at 37° C. and 5% CO$_2$. At 1 hr intervals, both the optical density and the number of relative light units (RLU) from a 1 ml culture volume were determined. The curves of RLU vs OD$_{600}$ were plotted.

Figure 7:
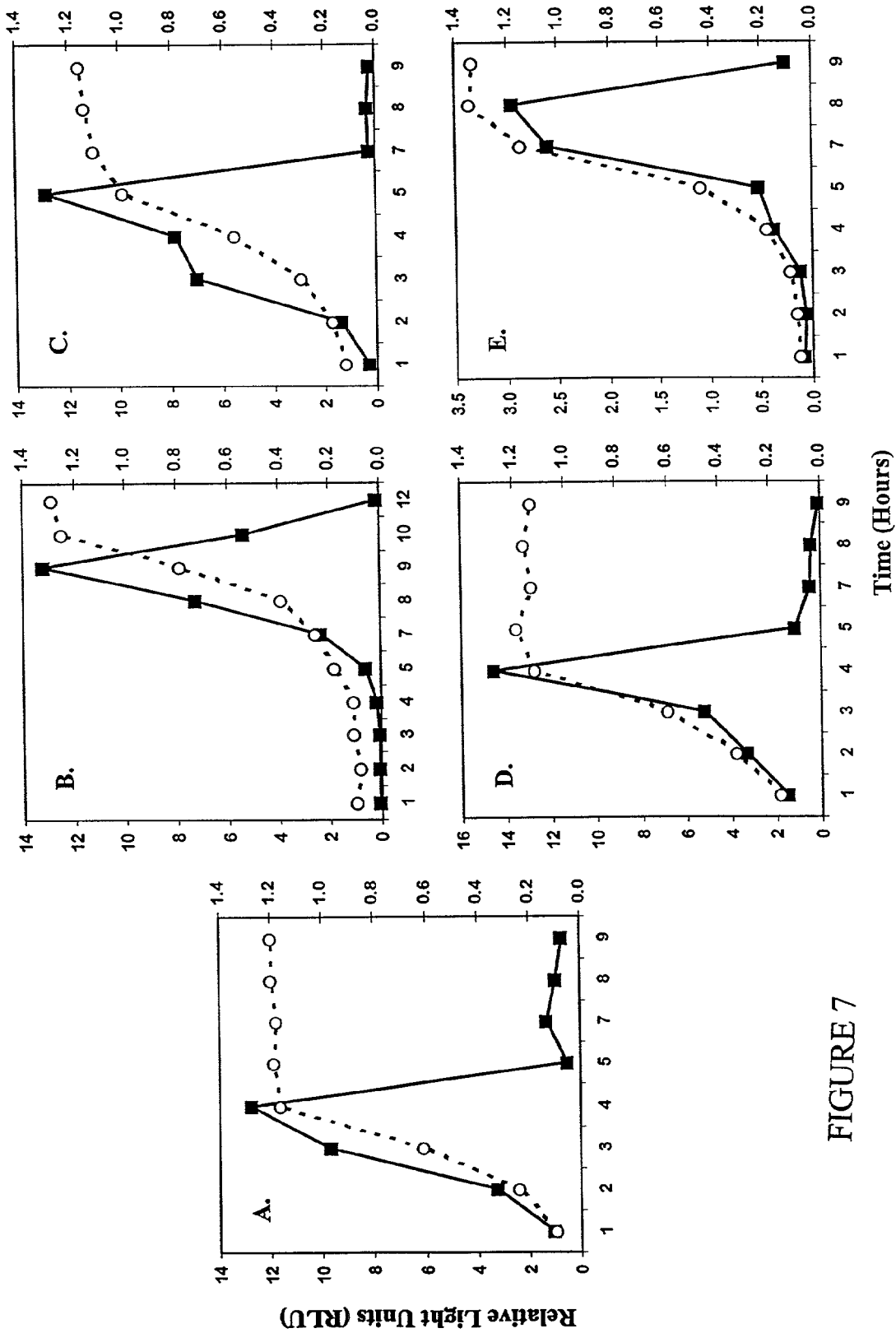
FIG. 7, panels A-E, are graphs depicting relative light units (RLUs) emitted by bioluminescent S. pneumoniae strains during in vitro growth. Three hundred microliters of overnight culture was inoculated in 30 ml BHI and grown at 37° C. and 5% $CO_2$. At 1 hr intervals, both the optical density (OD 600 nm, open circles ○) and the number of relative light units (RLUs in million units, solid squares ■) from a 1 ml culture volume were determined for each of the specified strains.

In all five strains the photon counts increased during exponential growth and then decreased dramatically to about 5% of their peak values once the bacteria entered stationary phase (FIG. 7). For strain Xen 11, the peak photon counts were less than those recorded from the other strains, which might be reflective of strain variation. This reasoning is supported by the observation that EF3030 Xen 11 showed a different hybridization pattern in a Southern blot analysis compared to the donor strain Xen 7 and the other transformed strains, Xen 9, Xen 10 and Xen 12. Despite these differences, inverse PCR showed that the transposon in Xen 11 was integrated at the same site as it was in the other strains. This integration site is located in a second ORF of a possible two-gene operon. Unfortunately the sequence of this ORF has no significant similarity at the DNA or protein level to any deposit in the NCBI database.

To investigate whether the stationary phase phenomenon described above was due to the regulation of one specific promoter or was a true consequence of the growth phase of S. pneumoniae, 10 different bioluminescent transposants were randomly picked from chocolate plate supplemented with kanamycin and their RLUs were measured during growth. In all the cases, the RLUs were significantly reduced to basal levels when stationary phase was reached, suggesting that the reduction of photon emission was a stationary phase phenomenon in S. pneumoniae.

Bioluminescent S. pneumoniae A66.1 Xen 10 Can be Used to Accurately Monitor Pneumococcal Drug Efficacy Studies in Vivo in Living Animals.

Initial studies with S. pneumoniae D39 Xen 7 showed this strain to perform poorly in animal infection studies due to its rapid clearance from the mice. Thus, the strains HUSTM-BIG, A66.1, EF3030 and 140301 were made bioluminescent and tested in both mouse lung and nasopharyngeal models. Briefly, exponential cultures of S. pneumoniae grown at 37° C. in BHI were pelleted and then resuspended in fresh BHI broth. Bacterial concentrations were estimated spectrophotometrically by absorbance at 600 nm and adjusted to approximately $10^7$ CFU/ml by dilution BHI. Cell numbers were verified by plating dilutions of inoculum onto BHI agar.

Pneumococci were introduced into the lungs of the mice by either direct intratracheal inoculation, or by intranasal administration. The animals were anesthetized with ketamine (100 mg/ml) and xylazine (20 mg/ml), mixed at a 4:1 ratio v/v just before use. The anesthesia mixture was injected intramuscularly into the right hamstring muscle at a dose of 100 mg ketamine/kg of body weight. After anesthesia was established, the mice were inoculated with approximately $10^6$ CFU in a total volume of 20 µl, using a 25 ga. Ball-tipped gavage needle. Mice were held in vertical suspension for 10 minutes after inoculation to facilitate deep penetration of the inoculum. Alternatively, mice were infected intranasally with approximately $10^6$ CFU by placing 20 µl of bacterial suspension on the nares and allowing the mice to inhale the inoculum. In the antibiotic studies, mice were treated with amoxicillin at 1 mg/kg or 5 mg/kg, given subcutaneously at t=0, 18, 24, and 42 hours post-infection.

Mice were imaged for a maximum of 5 min at a number of time points post-infection using an IVIS™ CCD camera (Xenogen Corporation, Alameda, Calif.). Total photon emission from selected and defined areas within the images of each mouse was quantified using the LivingImage™ software package (Xenogen Corporation, Alameda, Calif.). The photon signal from the thorax was quantified from the ventral image of each mouse.

A66.1 Xen 10 was found to perform best in the mouse pneumococcal lung model, whereas HUSTMBIG Xen 9 and EF3030 Xen 11 performed best in the nasopharyngeal model. Similar to D39 Xen 7, the strain 140301 Xen 12 did not perform well in either model.

Since A66.1 Xen 10 performed best in the mouse pneumococcal lung model, this strain was selected to test in a drug efficacy study. Twelve mice were inoculated with approximately $10^6$ CFU of S. pneumoniae A66.1 Xen 10. The mice were divided into three groups of four animals and two of these groups were treated with an amoxicillin regime at 1 or 5 mg/kg, the third group of animals remaining untreated as controls. In the untreated group of animals, a strong bioluminescent signal could be detected from the thorax of three of the four mice by 20 hr, indicating three of the mice to have an established pneumococcal lung infection. These animals all had ruffled fur and appeared ill, whereas the fourth control animal, showing no bioluminescent signal, appeared healthy. Over the next 28 hr (up to 48 hr post-inoculation) the three infected control animals showed increasing bioluminescent signals from their lungs (FIG. 8), the mouse with the highest signal at 26 hr dying overnight before the 44 hr imaging time-point. By 48 hr post-inoculation at least one of the two remaining infected mice appeared extremely ill, with both animal having bioluminescent signals that were so bright that they rapidly (<30 s) saturated the camera's detection limit.

Figure 8:
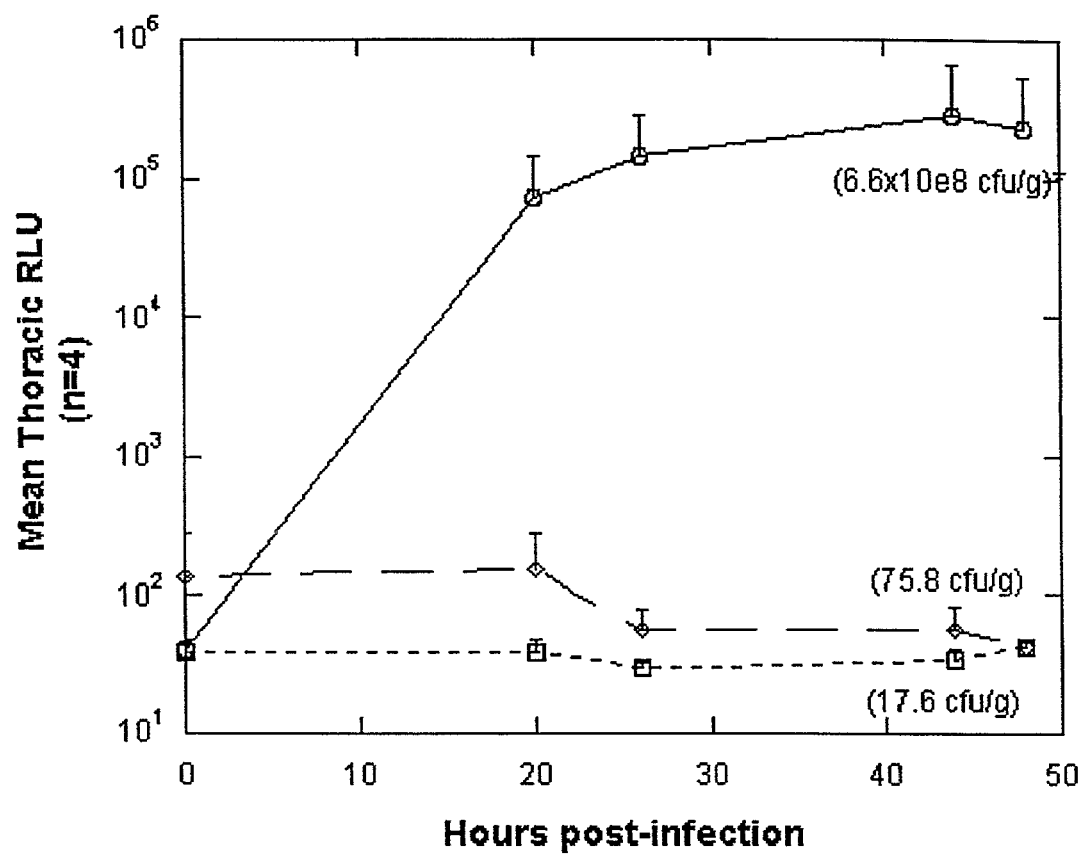
FIG. 8 is a graphical representation of mean thoracic bioluminescence (RLU) from pneumococci infected mice, untreated and treated with amoxicillin. Each point represents the average bioluminescence from all surviving mice in each treatment group (starting at n=4 in each case). open circles ("○") show untreated animals; open squares ("□") show 5 mg/kg amoxicillin treated animals; open diamonds ("◊") shows 1 mg/kg amoxicillin treated animals. Average CFU/g lung tissue for each group of animals at time 48 hr is given in parentheses.

All eight of the amoxicillin (1 and 5 mg/kg groups) treated mice appeared relatively healthy at the 20 hr imaging time-point. Three of the four 1 mg/kg amoxicillin treated animals had a bioluminescent signal 20 hr post-inoculation. None of the four 5 mg/kg amoxicillin treated animals had a significant bioluminescent signal at this time-point. In comparison, the group of untreated control animals developed an intense bioluminescent signal (FIG. 8).

After the final imaging time point, mice were sacrificed and the infected lung tissue was surgically removed and weighed. Both lungs were homogenized together in 500 µl BHI in a loose Dounce homogenizer. The suspension was serially diluted in BHI and plated in duplicate onto BHI agar. Bacterial burden was estimated from the number of CFU/g of lung tissue. The bacterial load present in the nasal passage of the mice was obtained by washing approximately 0.25 ml of saline through the trachea and collecting the first 0.1 ml of nasal wash as it exited the nares, as described (Lipsitch et al. (2000) Vaccine 18:2895–2901; Wu et al. (1997) Microb. Pathog. 23:127–137).

Plating of lung tissue from each of the mice after the final 48 hr imaging time-point, showed only the two untreated animals with strong bioluminescent signals to have high numbers of pneumococcus present, one of these animals having $2 \times 10^9$ CFU/g tissue. No bacteria could be recovered from the untreated mouse that did not have a bioluminescent signal, supporting the assumption that in this host a pneumococcal infection had not been established. The highest number of pneumococci to be isolated from an amoxicillin treated animal was 300 CFU/g tissue, with four of the eight animals showing no bacteria present.

All pneumococcus recovered from long-term mouse nasopharyngeal infections are bioluminescent. S. pneumoniae HUSTMBIG Xen 9 and EF3030 Xen 11 recovered from nasal washes performed on mice with seven day pneumococcal nasopharyngeal infections, were shown to be 100% bioluminescent. Furthermore, Southern blot analysis of genomic DNA recovered from a number of these bacteria showed that the lux transposon was inserted at its original location and was still a single copy.

Thus, integration of the lux operon into the chromosome of S. pneumoniae D39 using pAUL-A Tn4001 luxABCDE $km^R$ not only stabilized the bioluminescent signal, it also allowed lux fusions to be selected by their phenotype (e.g., bioluminescence, growth rate and virulence in animals) as opposed to being intuitively constructed (e.g., promoter sequence selected from published data, amplified by PCR and fused to lux), then tested. This former phenotypic screening approach, enabled a variety of constitutive, highly bioluminescent strains to be rapidly identified and tested for virulence in vivo in animals. Initial studies with bioluminescent S. pneumoniae D39 (mostly Xen 7) showed that it was possible to monitor pneumococcal cells in vivo in a mouse thigh model. As described herein, S. pneumoniae A66.1 Xen 10 performed extremely well in the lungs of mice (FIG. 8) making it a good candidate for in vivo pneumococcal drug efficacy studies. The strains described herein (e.g., Streptococcal strains such as HUSTMBIG Xen 9 and EF3030 Xen 11, which performed best in the mouse nasopharyngeal model) as well as other gram-positive organisms, can provide valuable information for vaccination studies due to their longevity of colonization of the nasal passage.

Both of the pneumococcal animal models described herein demonstrate the tremendous advantages that real-time photonic imaging offers over conventional methods for monitoring and combating bacterial disease in animals. Not only does this approach reduce the time and cost of conducting such experiments, but it also considerably reduces the number of animals used (Contag et al. 1995). Furthermore, because bioluminescent imaging allows the same group of animals to be monitored over time, animal-to-animal variations are overcome by including the zero time point as an internal control. In addition to this procedure improving biostatistics, several parameters of drug efficacy and pharmacokinetics can be more accurately measured in the discovery and development stages of drug evaluation.

EXAMPLE 15

Use of Transposon LTV1-Tn917 luxABCDE to Engineer Bioluminescent MRSA

As an alternative to transposon Tn4001 luxABCDE km$^R$ construct, modified transposon Tn917 was prepared for use in engineering of bioluminescent methicillin-resistant *S. aureus* (MRSA).

Figure 9:
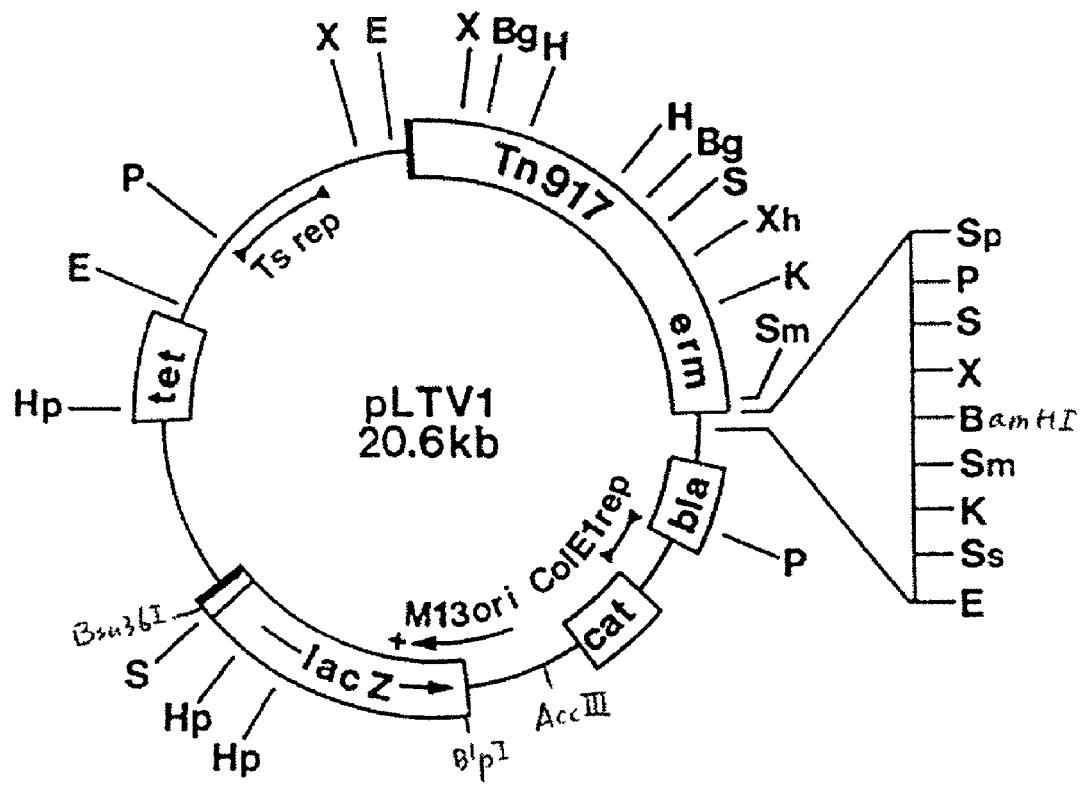
FIG. 9 is a schematic depicting the construct designated pLTVI.

The plasmid pLTV1-Tn917 (Camilli et al., 1990 J. Bacteriol. 172:3738–44; Watson et al., 1998 Microbiology 144: 3159–69; Schwan et al., 1998 Infect Immun. 66:567–72; Sebulsky et al., 2000 J Bacteriol. 182:4394–400; Eichenbaum and Scott, 1997 Gene 186:213–7); Mansilla and Mendoza, 1997 J Bacteriol. 179:976–81; Tran et al., 2000 Mol Microbiol 37:1159–71) is depicted in FIG. 9.

An *E. coli* strain HB101 containing plasmid pLTV1-Tn917 was purchased from *Bacillus* Genetic Stock Center (Ohio State University). The plasmid was prepared from *E. coli* using Qiagen mini-prep column and transformed into competent *S. aureus* strain RN4220 using electroporation protocol described above. The transformation mixture was plated on BHI plates supplemented with 5 µg/ml erythromycin and then incubated at 30° C. for 24–48 hours. A single colony of RN4220 transformant containing plasmid pLTV1-Tn917 was inoculated in 10-ml BHI medium supplemented with 5 ug/ml erythromycin (erm5) and 15 µg/ml tetracycline (tet15). The culture was incubated at 37° C. at 200 rpm overnight. Then the culture was diluted 1:20 in fresh BHI medium with erm5 and grown at non-permissive temperature of 43° C. at 200 rpm to OD600 of 0.8. The culture was diluted 1:20 again in fresh BHI medium with erm5 and grown at 43° C. at 200 rpm overnight. The overnight culture was diluted $10^{-1}$ to $10^{-6}$ and each dilution was plated on BHI plate erm5, cm5 (5 ug/ml chloremphenicol), and tet15 respectively. After the plates were incubated at 45° C. overnight, total colonies on each plate were counted. An estimated 80% of the colonies showed em$^R$ cm$^R$ tet$^S$ that indicated the transposition of Tn917 onto *S. aureus* chromosome and the loss of plasmid pLTV1 backbone containing tetracycline resistant marker. A total of 40 colonies grown on BHI with erm5 plate were patched onto fresh BHI plate with erm5, cm5, and tet15 respectively and incubated at 45° C. overnight. All 40 colonies were grown on both erm5 and cm5 plates, and only 7 were grown on tet15 plate.

The results indicated that the chloremphenicol resistant cassette worked when integrated on chromosome and the Tn917 transposition occurred in 83.5% of the colonies tested under the above-described culture conditions. The MRSA strain I6 is resistant to all the antibiotics tested except for chloremphenicol. Thus, plasmid pLTV1-Tn917 and its derivatives can be used for engineering of I6 and other MRSA strains.

The modified Gram positive luxABCDE or luxABCDE kan$^R$ operon described in previous sections was cloned into pLTV1-Tn917 in two ways. First, a 3.0 kb Bsu36I/BlpI fragment containing lacZ was removed and then replaced by Gram-positive luxABCDE operon or luxABCDE kan$^R$. Upon transposition, the expression of luxABCDE operon or luxABCDE kan$^R$ depends on the insertion of transposon downstream of a promoter in the chromosome of the target organism. Second, the luxABCDE operon or luxABCDE kan$^R$ is operatively linked with a known promoter (such as, P3 promoter for RNAIII at agr locus, or pts promoter). The location of the promoter is typically 5' of luxA. This promoter containing construct is cloned into the unique BamHI site in the multiple cloning site in pLTV1-Tn917ΔlacZ as described above, or cloned into the Bsu36I/BlpI site of pLTV1-Tn917. The luxABCDE operon or luxABCDE kan$^R$ is expressed from the known promoter and the expression of lux operon is independent of the transposon integration site.

Once the luxABCDE operon or luxABCDE kan$^R$ with or without the known promoter is integrated onto chromosome of *S. aureus* strain (such as RN4220), the luxABCDE operon, alone with kan$^R$ or cm$^R$ antibiotic resistant marker, can be transferred to other *S. aureus* strains (such as MRSA I6) by protoplast fusion or phage transduction. The transformants or transductants can be selected as light colonies on appropriate antibiotics plates.

Although preferred embodiments of the subject invention have been described in some detail, it is understood that obvious variations can be made without departing from the spirit and the scope of the invention as defined by the appended claims.

---

What is claimed is:

1. A vector comprising,
   (a) a vector backbone comprising at least one polynucleotide sequence encoding light generating polypeptide sequences operably linked to a promoter functional in a target organism of interest and
   (b) a transposon cassette comprising a polynucleotide sequence comprising
      an internal polynucleotide sequence, said internal polynucleotide sequence comprising (i) a first sequence of interest encoding at least one light generating polypeptide sequence, said first sequence present in a first orientation, capable of being expressed in a gram-positive target organism and lacking control sequences that are capable of promoting transcription in the target organism and (ii) a transposase coding sequence operably linked to a promoter functional in the target organism, wherein said transposase coding sequence is in a second orientation relative to polypeptide coding sequences of the first sequence of interest encoding polypeptide sequences, and said transposase is capable of inducing transposition mediated by transposon inverted repeats; and
      first and second transposon inverted repeat sequences, wherein said first and second transposon inverted repeat sequences (i) are from a gram-positive bacterium; and (ii) flank said internal polynucleotide sequence;
   wherein said promoter in said vector backbone does not affect transcription of any coding sequences in the transposon cassette.

2. The vector of claim 1, wherein said first and second transposon inverted repeat sequences, and said transposase coding sequence are derived from Tn4001.

3. The vector of claim 1, wherein said vector backbone further comprises a transposase coding sequence operably linked to a promoter functional in the target organism, said transposase capable of inducing transposition mediated by said transposon inverted repeats and wherein said promoter operably linked to said transposase coding sequence in said vector backbone does not affect transcription of any coding sequences in the transposon cassette.

4. The vector of claim 1, wherein said transposon cassette contains a polynucleotide sequence encoding light generating polypeptide sequences wherein light generating polypeptide produced from coding sequences within the transposon cassette produce bioluminescence of a characteristic first wavelength that is detectably different from a characteristic second wavelength of bioluminescence produced by the product of the polynucleotide sequence encoding light generating polypeptide sequences contained within the backbone vector.

5. The vector of claim 1, wherein said polynucleotide sequence encoding light generating polypeptide sequences comprises a polynucleotide selected from the group consisting of: (a) a polynucleotide encoding luxA, and luxB gene products; (b) a polynucleotide encoding luxA, luxB, luxC, luxD and luxE gene products; (c) a polynucleotide encoding luxY gene product; and (d) a polynucleotide encoding luc gene product.

6. The vector of claim 1, wherein the vector backbone comprises: (i) a Gram-negative origin of replication; (ii) a Gram-positive origin of replication; and (iii) a selectable marker coding sequence operably linked to a promoter functional in the target organism, wherein said promoter operably linked to said selectable marker does not affect transcription of any coding sequences in the transposon cassette.

7. The vector of claim 1, wherein said vector backbone is pAUL-A.

8. The vector of claim 1, said vector backbone comprising an origin of replication that is functional in more than one target host cell.

9. The vector of claim 8, wherein said origin of replication is functional in both Gram-negative and Gram-positive cells.

10. The vector of claim 1, further comprising at least one transcription termination sequence in the vector backbone and adjacent the transposon cassette, such that said transcription termination sequence essentially prevents transcription originating from any promoter present in the vector from reading through into the transposon cassette sequences.

11. The vector of claim 10, comprising two transcription termination sequences in the vector backbone wherein said transcription termination sequences flank the transposon cassette, such that said transcription termination sequences essentially prevent read-through transcription originating from any promoter present in the vector into the transposon cassette sequences.

12. The vector of claim 1, wherein said vector backbone further comprises a selectable marker sequence of interest operably linked to a promoter functional in a target organism, wherein said promoter does not affect transcription of any coding sequences in the transposon cassette.

13. The vector of claim 12, wherein said selectable marker coding sequence is a polynucleotide sequence encoding a polypeptide conferring antibiotic resistance.

14. The vector of claim 13, wherein said selectable marker coding sequence is a polynucleotide sequence encoding a polypeptide conferring antibiotic resistance, said antibiotic being selected form the group consisting of actinomycin, ampicillin, chloramphenicol, erythromycin, gentamycin sulfate, hygromycin, kanamycin, neomycin, penicillin, polymixin B sulfate and streptomycin sulfate.

15. The vector of claim 1, said vector backbone comprising an origin of replication that is functional in a target host cell.

16. The vector of claim 15, wherein said vector backbone comprises a Gram-negative origin of replication.

17. The vector of claim 6, wherein said Gram-negative origin of replication is conditional.

18. The vector of claim 15, said vector backbone comprises a Gram-positive origin of replication.

19. The vector of claim 18, wherein said Gram-positive origin of replication is conditional.

20. The vector of claim 19, wherein said conditional Gram-positive origin of replication is temperature-sensitive.

21. A cell carrying the vector of claim 1.

22. A cell produced by a method comprising the steps of transforming said cell with the vector of claim 1; and
culturing the transformed cell under conditions that facilitate transposition of the transposon cassette from the vector into the genome of said cell.

* * * * *